United States Patent [19]
Young et al.

[11] Patent Number: 5,788,673
[45] Date of Patent: Aug. 4, 1998

[54] DRUG INFUSION SYSTEM

[75] Inventors: Larry Lee Young, Arab; Richard Rabenau, Birmingham; Stephen Perry Lisak, Arab; Rowland William Kanner, Guntersville, all of Ala.

[73] Assignee: Atrion Medical Products, Inc., Arab, Ala.

[21] Appl. No.: 461,857

[22] Filed: Jun. 5, 1995

[51] Int. Cl.$^6$ .................................................. A61M 37/00
[52] U.S. Cl. ............................................. 604/131; 604/134
[58] Field of Search .................................. 604/131, 133, 604/134, 135, 150, 154

[56] References Cited

U.S. PATENT DOCUMENTS

| | | | |
|---|---|---|---|
| Re. 32,922 | 5/1989 | Levin et al. | 604/131 X |
| 3,474,787 | 10/1969 | Grant | 604/135 |
| 4,112,947 | 9/1978 | Nehring | 604/131 X |
| 4,180,067 | 12/1979 | Derlien | 604/131 |
| 4,623,330 | 11/1986 | Laby et al. | 604/131 X |
| 4,795,433 | 1/1989 | Sarnoff | 604/134 |
| 4,820,286 | 4/1989 | Van Der Wal | 604/134 X |
| 5,209,746 | 5/1993 | Balaban et al. | 604/131 X |
| 5,380,279 | 1/1995 | Schmidt | 604/131 X |

FOREIGN PATENT DOCUMENTS

| | | |
|---|---|---|
| 8101787 | 1/1991 | Australia . |
| 8802637 | 4/1988 | WIPO . |

*Primary Examiner*—John D. Yasko
*Attorney, Agent, or Firm*—Trexler, Bushnell, Giangiorgi & Blackstone, Ltd.

[57] ABSTRACT

A novel fluid infusion system utilizing a fluid pump device and a syringe is used in an intravenous or infusion application of a liquid product, such as a medication, to a patient. The pump device includes a housing that has a compartment for reception of at least a portion of the plunger of the syringe. A drive component is disposed in the compartment and is relatively movable with respect to the housing for engaging and producing movement of the plunger. A fluid medium is contained within the housing and a relatively movable piston is in operative communication with the fluid medium and a biasing structure is provided for biasing the piston in a first direction to impart a force on the fluid medium. A metering orifice is in communication with the fluid medium and through which the medium can pass upon movement of the piston in the first direction to restrict and control the flow of the medium. Valve structure for the fluid medium permits the rapid return movement of the piston in a second direction opposite the first direction. The piston is operatively associated with the drive component, such that the movement of the piston in the first direction is transferred to the drive component with the metering orifice in effect controlling the rate of movement of the piston and the drive component and correspondingly the movement of the plunger thereby controlling the rate of expulsion of the liquid product from the syringe.

66 Claims, 9 Drawing Sheets

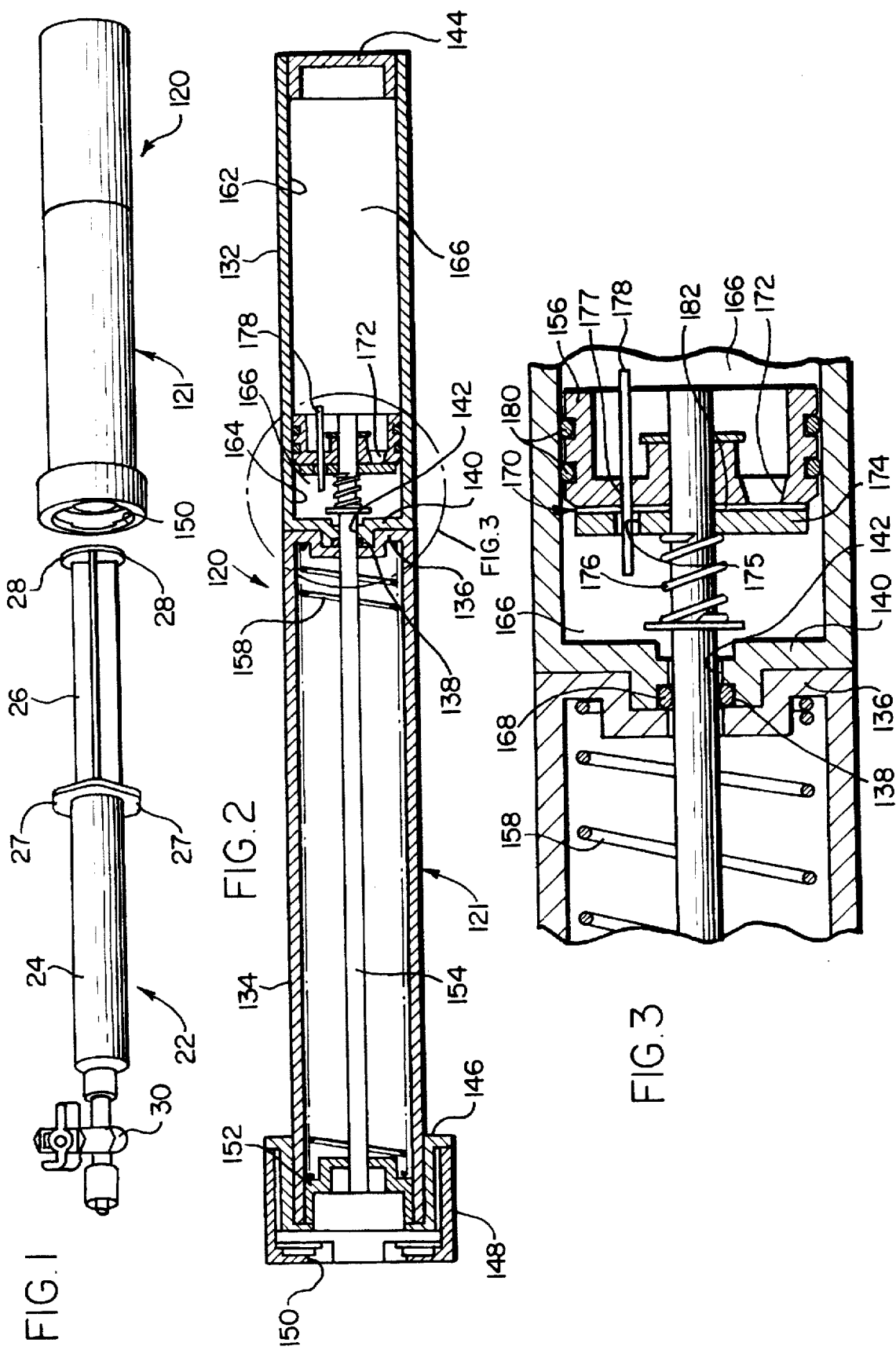

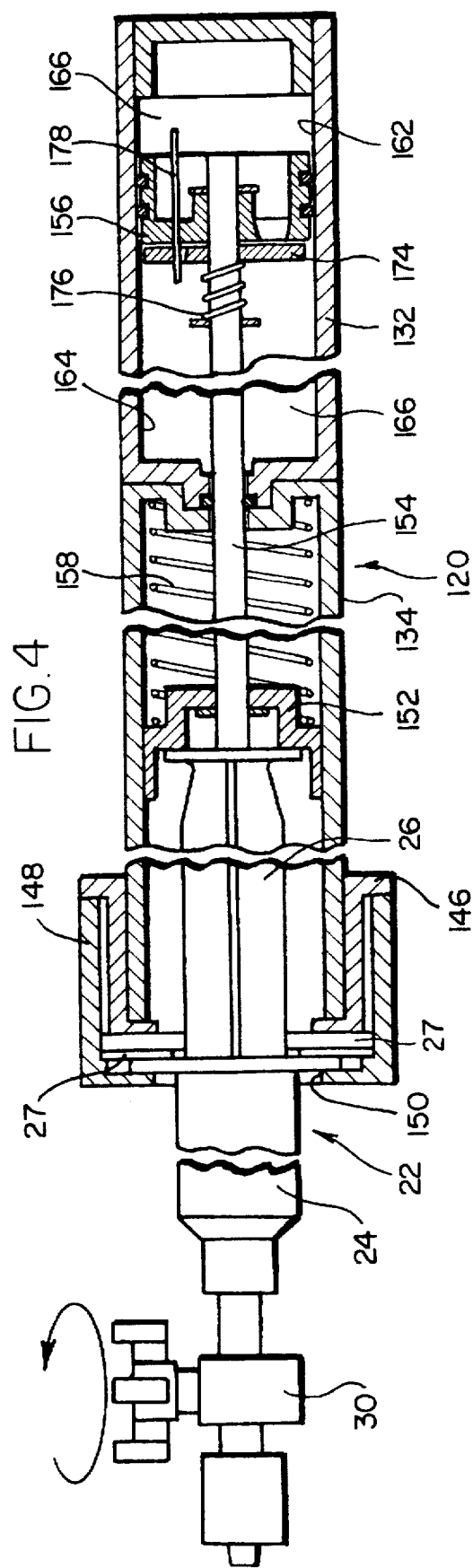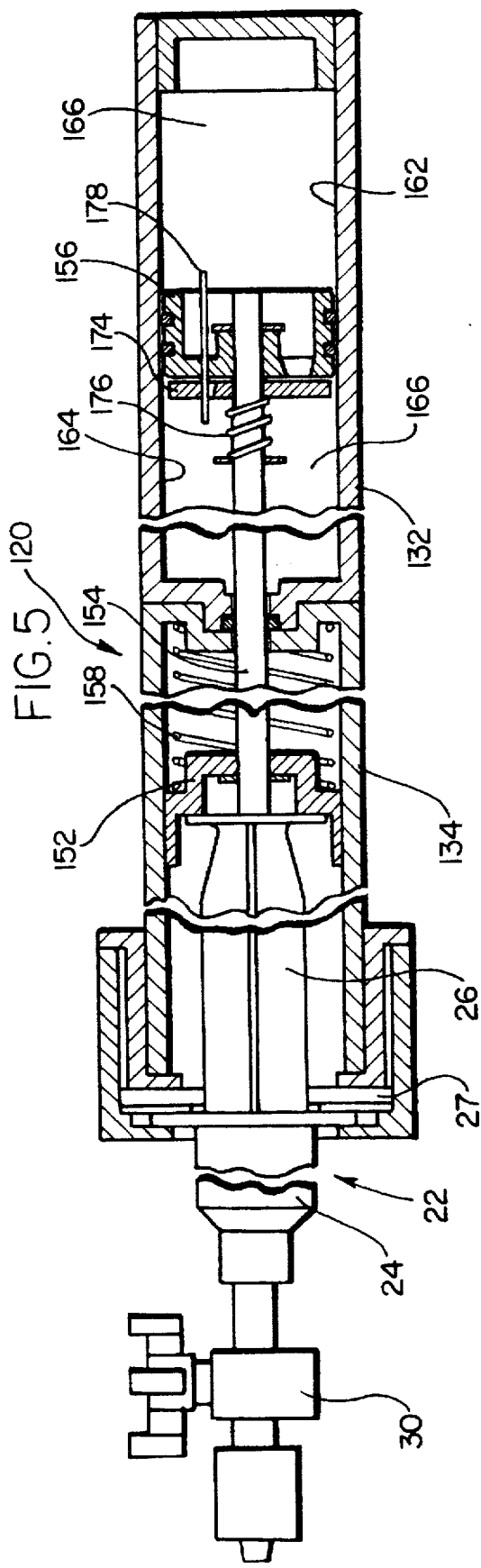

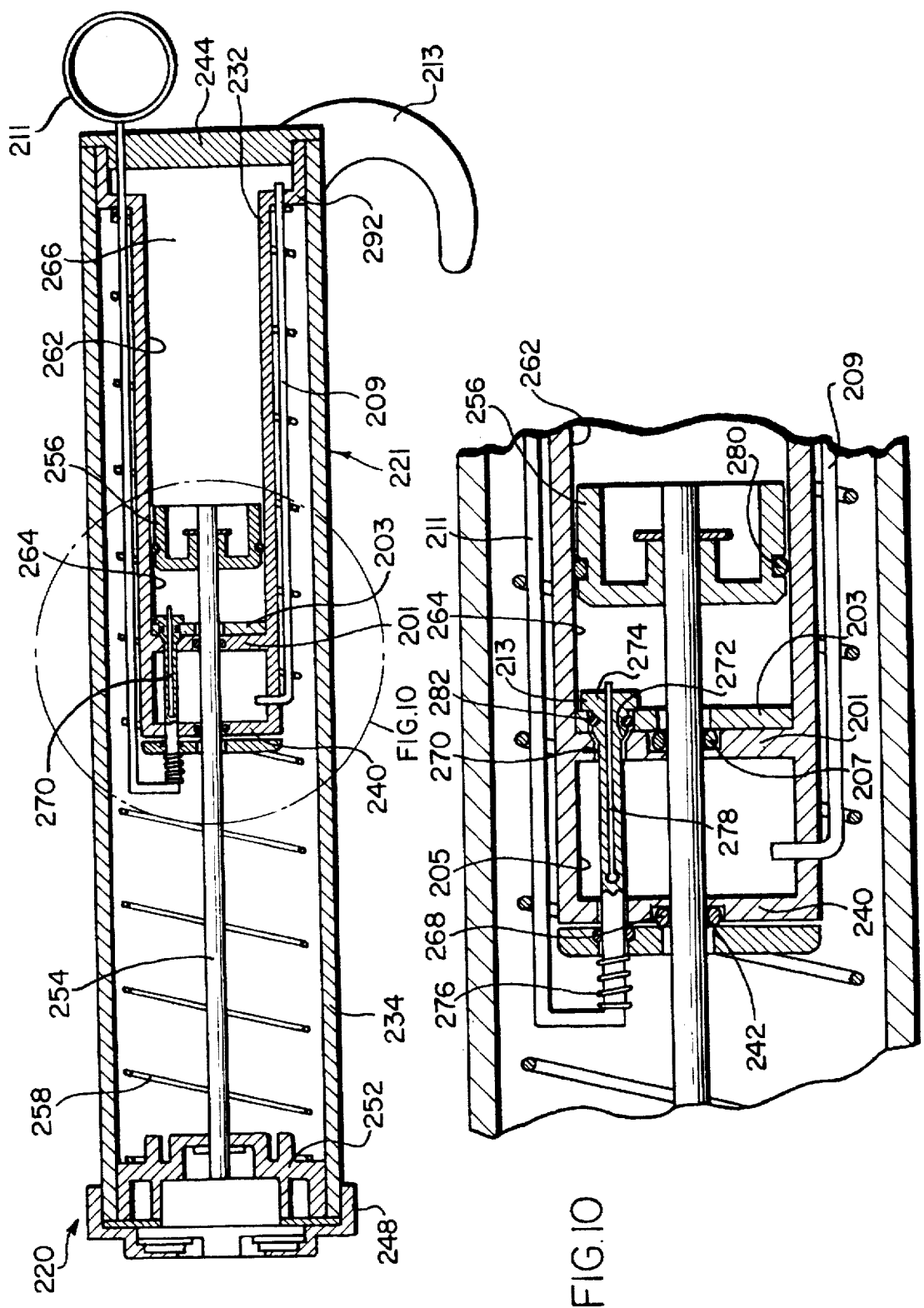

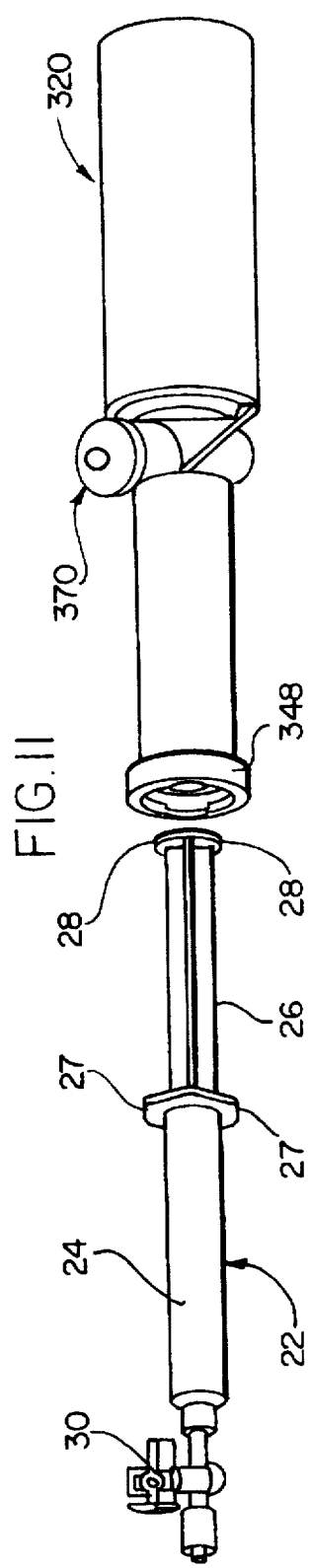
FIG.11
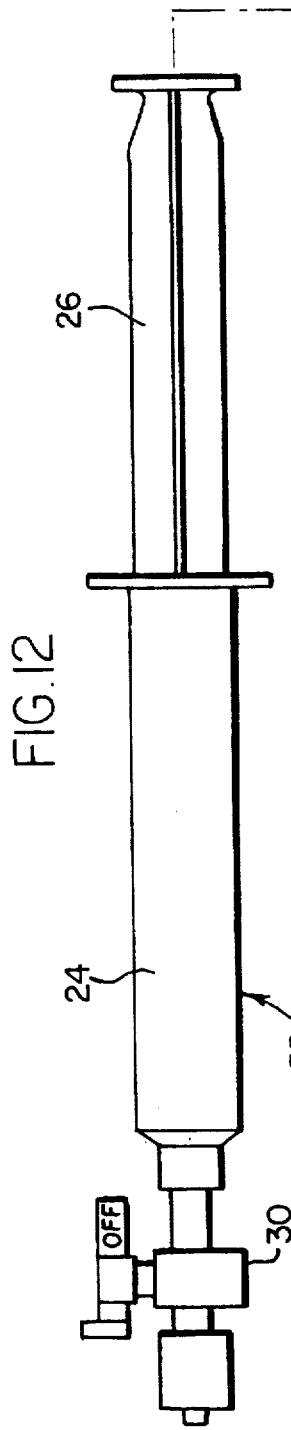
FIG.12
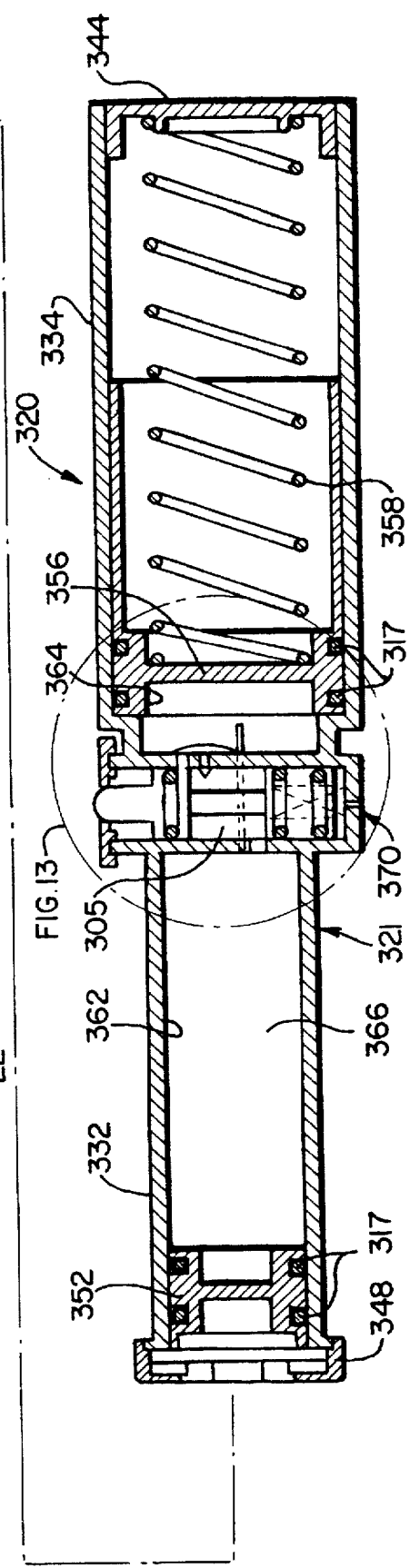

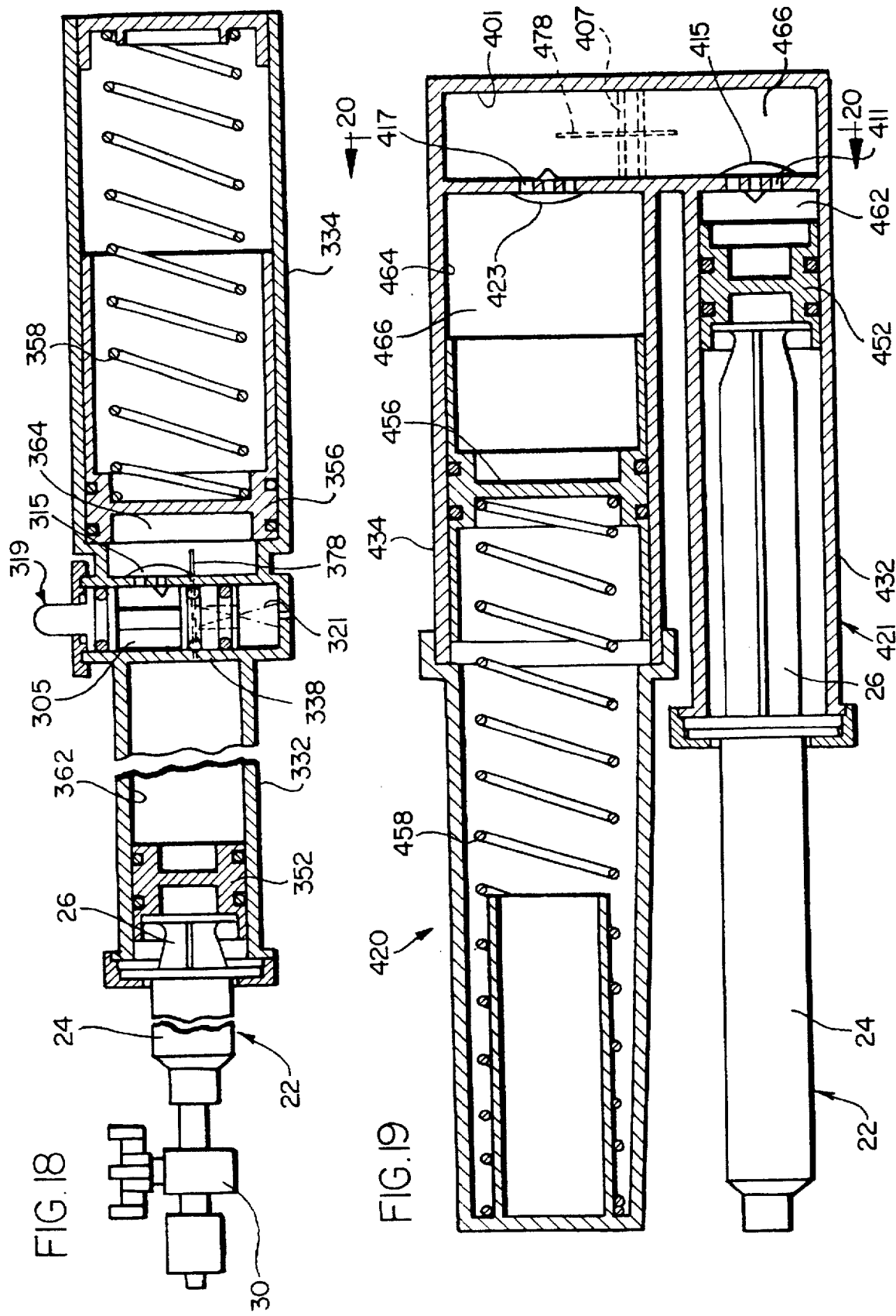

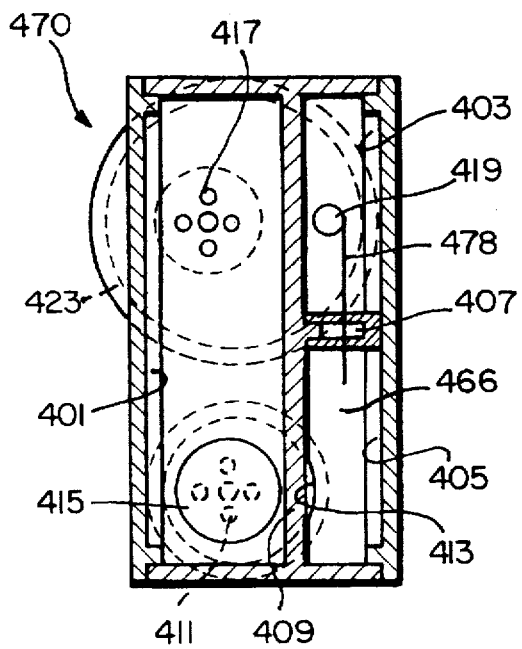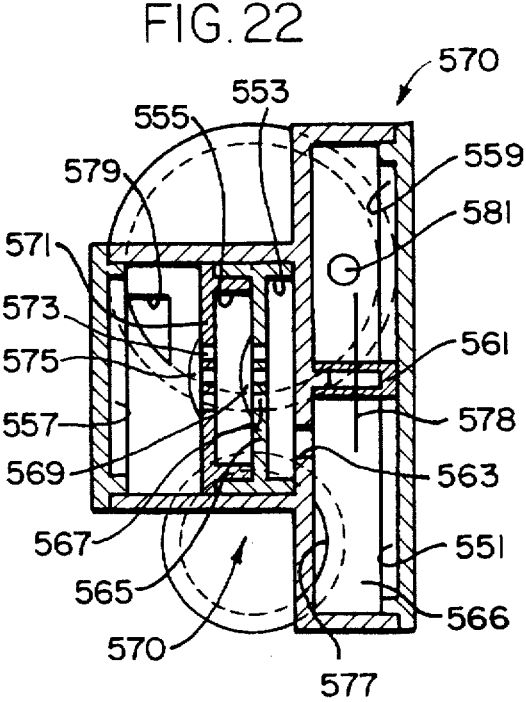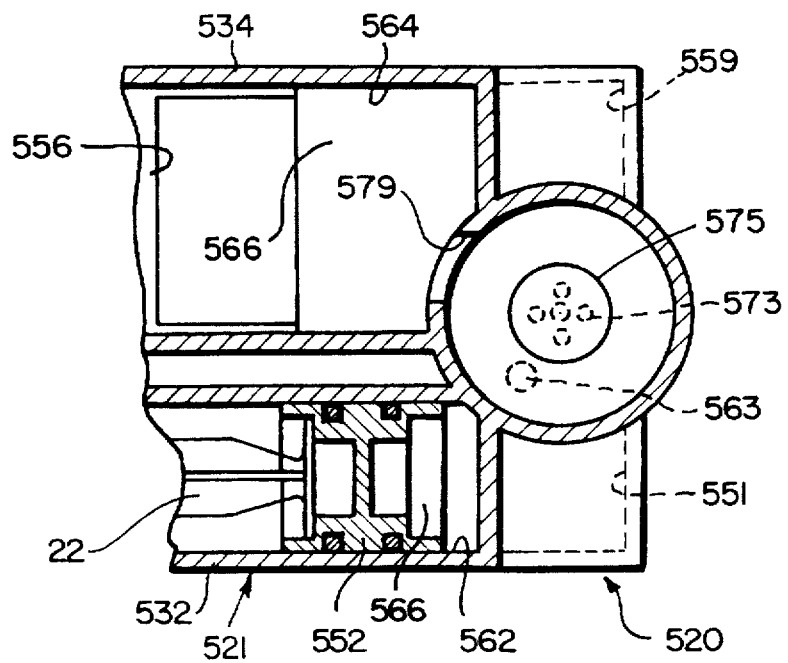

DRUG INFUSION SYSTEM

BACKGROUND OF THE INVENTION

This invention is generally directed to a novel fluid infusion or pump device which is used to dispense a drug or medication from a syringe to a patient at a predetermined rate over a predetermined time period. More particularly, the system of the invention contemplates an a fluid infusion device and syringe combination that does not rely on the characteristics of the drug to dispense the drug from the syringe.

Commonly, to take medication, a patient ingests the medication in a pill form. A problem that occurs when medication is taken in this form is that a sinusoidal delivery of the medication to the bloodstream of the patient occurs and thus, the effects of the medication varies over time. To reduce this effect, it is desired that an even delivery of the medication is supplied to the patient. To do this, however, the patient must receive the medication intravenously over a predetermined time period.

In an intravenous delivery of medication, a patient is usually connected to an IV bag on a pole by a metered infusion pump. Usually, the patient must be confined to a bed in a hospital or at home. The structure which is required to deliver the medication is bulky and expensive and typically cannot be easily moved. This does not allow the patient-to be ambulatory while still receiving the necessary medication. This method of receiving medication is not acceptable for patients who need to receive medication on a day-to-day basis on a constant or intermittent basis, such as diabetics or cancer patients.

One system which attempts to provide a structure for allowing a person to be ambulatory while still receiving the necessary medication is disclosed in Australian Patent Document No. AU-B-81017/87. This system feeds the medication from a syringe through a resistance tubing to the patient by pressure from a fluid filled balloon or a compression spring. The length and diameter of the resistance tubing, along with the characteristics of the fluid medication, dictate the rate of flow of medication through the resistance tubing and thus, the rate of delivery of the medication to the patient.

One problem that occurs with this type of system is that different medications vary in characteristics, such as the viscosity of the fluid, which can change based on the room temperatures. Therefore, a different resistance tube must be used for each medication which is to be dispensed since the rate of delivery is dependent on the medication being fed through the resistance tube to the patient. This must be carefully calculated each time a different medication is to be dispensed.

The present invention presents a novel fluid infusion system including an infusion pump and syringe, which is not dependent on the characteristics of the medication nor the diameter and length of a section of metering tubing to deliver a controlled rate of flow of the medication to a patient. Instead, the present invention relies on known factors or parameters, which can be easily and reliably changed to vary the rate of delivery of medication to a patient. The present invention presents several other advantages and improvements over the prior art which will be clear upon a reading of the disclosure herein.

More specifically, the present invention provides an infusion pump device that can be used with a syringe to provide controlled application of a liquid medication. In this regard, syringes come in varying sizes or capacities, which constitute a known factor or parameter. The infusion pump device includes a housing for receiving at least the plunger member of the syringe and the pump further includes a self contained fluid medium. The fluid medium is movable under pressure across a barrier by means of a delivery or metering orifice such as by means of a biased piston member. The piston member could be spring biased or biased by a compressed gas or any other biasing means. As such, a predetermined rate of movement of the piston member may be calculated and attained by varying several known, and easily controllable factors, such as the biasing force, the size of the metering orifice, the area of the piston and the viscosity of the fluid medium. In addition, the diameter of the syringe needle can be varied to control the rate that the liquid product is dispensed from the syringe. By adjusting these parameters it is possible to determine that the piston will attain a known amount of movement over a given period of time. Further, the infusion pump device may include a drive component within its housing that is linked or operably connected to the piston for associated movement. Thus, the rate of movement of the drive component can also be determined and controlled. The drive component in turn engages and will depress the plunger member of a syringe and this movement will take place at the previously predetermined rate, equal to or a whole or fractional multiple of the rate of movement of the piston. Further, since the volume of liquid medication drawn into the syringe is known, the flow rate of the medication from the syringe is easily determined and controlled, depending on the parameters of the infusion pump device and system.

OBJECTS AND SUMMARY OF THE INVENTION

A general object of the present invention is to provide a novel infusion system and apparatus and method of dispensing or infusing liquid medication or other fluids to a patient in a controlled manner.

An object of the present invention is to provide an ambulatory infusion system which reliably dispenses or infuses a drug at a predetermined rate over a predetermined time period.

Another object of the present invention is to provide a portable system for delivering or infusing medication to a patient at a controlled rate.

Briefly, and in accordance with the foregoing, the present invention discloses a novel fluid infusion system of which is capable of being used in an intravenous application of a liquid product, such as a drug or medication, or infusion of a liquid product into a muscle or the like, while systematically employing a novel infusion pump design and syringe. The fluid infusion device pump includes a housing that has a compartment for reception of at least a plunger portion of the syringe and a drive component which is relatively movable with respect to the compartment for engaging the syringe plunger and producing movement thereof. A fluid medium of known quantity and fluid flow characteristics is contained within a portion of the housing. A relatively movable piston in operative communication with the fluid medium and biasing means in the form of a spring or the like, is provided for biasing the piston in a first direction of movement to impart a force upon or to pressurize the fluid medium. A metering orifice is in communication with the fluid medium through which the fluid medium can pass upon movement of the piston in the first direction. The orifice may be in the form of a tubular member. The metering orifice restricts and controls the rate of flow of the fluid medium upon movement of the piston in the first direction. Valve structure for the fluid medium is provided to permit the rapid return movement of the piston in a second direction opposite the first direction, which return movement is employed to reset or cock the pump device for the next operation. The piston is operatively associated with the drive component, such that the movement of the piston in the first direction is transferred to movement of the drive component with the metering orifice in effect controlling the rate of movement of the piston and the drive component and correspondingly the movement of the plunger engaged by the drive component, thereby controlling the rate of expulsion of the liquid product or medication from the syringe. The manner of operative association of the piston with the drive component may vary; there are shown several embodiments employing a direct connection, as well as an operative connection via the fluid medium.

BRIEF DESCRIPTION OF THE DRAWINGS

The organization and manner of the structure and operation of the invention, together with further objects and advantages thereof, may best be understood by reference to the following description, taken in connection with the accompanying drawings, wherein like reference numerals identify like elements in which:

FIG. 1 is a perspective view of a fluid infusion system which incorporates the features of a first embodiment of the invention;

FIG. 2 is a cross-sectional view of the first embodiment of the fluid infusion pump device without a syringe engaged therewith;

FIG. 3 is an enlarged cross-sectional view of the portion of the first embodiment of the fluid pump device shown in the circle in FIG. 2;

FIG. 4 is a cross-sectional view of the first embodiment of the fluid pump device with a syringe engaged therewith and in a fully cocked or ready position;

FIG. 5 is a cross-sectional view of the first embodiment of the fluid feed device with the syringe engaged therewith and in a partially depressed or expended position;

FIG. 9 is a cross-sectional view of a second embodiment of the fluid infusion device without a syringe engaged therewith;

FIG. 10 is an enlarged cross-sectional view of the portion of the second embodiment of the fluid pump device shown in the circle in FIG. 9;

FIG. 11 is a perspective view of a fluid infusion device which incorporates the features of a third embodiment of the invention;

FIG. 12 is a cross-sectional view of the third embodiment of the fluid infusion device with the syringe being shown in a side elevation;

FIG. 18 is a cross-sectional view of the third embodiment of the fluid infusion device with the syringe engaged therewith and in a fully expended position;

FIG. 19 is a cross-sectional view of a fourth embodiment of the fluid infusion device with a syringe engaged therewith and in a fully cocked or ready position;

FIG. 20 is a rear cross-sectional view of the fourth embodiment of the fluid infusion device shown in FIG. 19 taken along line 20—20;

FIG. 21 is a partial cross-sectional view of a fifth embodiment of the fluid feed device with a syringe engaged therewith and in a fully cocked or ready position; and FIG. 22 is a rear cross-sectional view of the fifth embodiment of the fluid infusion device shown in FIG. 21 taken along line 22—22.

DETAILED DESCRIPTION OF THE PREFERRED EMBODIMENT

Figure 6:
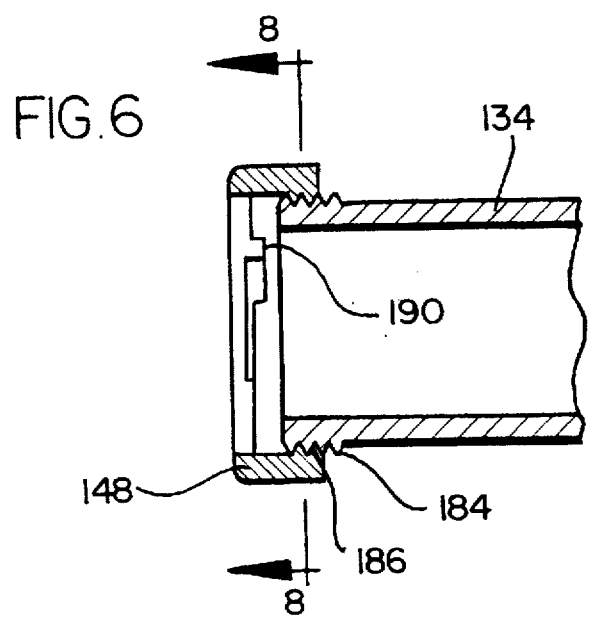
FIG. 6 is a cross-sectional view of an alternate structure for engaging or mounting the syringe to the fluid infusion device of the present invention.

While the invention may be susceptible to embodiment in different forms, there is shown in the drawings, and herein will be described in detail, specific preferred embodiments with the understanding that the present disclosure is to be considered an exemplification of the principles of the invention, and is not intended to limit the invention to that as specifically illustrated and described herein.

The novel drug infusion system includes a novel fluid feed or infusion pump device 120 capable of use in an intravenous application or infusion into a muscle application or the like for dispensing liquid medication or a liquid drug at a predetermined rate over a predetermined time period to a patient from a syringe. The drug infusion system of the present invention does not rely on the characteristics of the medication or drug itself to control the rate that the medication or drug is dispensed to the patient. Instead, the novel drug infusion system of the present invention uses structure that provides known parameters or factors which can be reliably and easily controlled to dispense the medication or drug to the patient at a predetermined flow rate.

The system of the present invention presents a significant advantage over the prior art in that the system is ambulatory. This allows a patient to have a greater amount of freedom in movement and lifestyles. The patient is not tied to a hospital bed and an I.V. pole and metering pump and instead, can live at home while still being able to take the prescribed medication.

The fluid feed or infusion device of the drug infusion system is used in combination with a syringe 22 which has known, predetermined flow characteristics, in that a predetermined amount of movement of the syringe plunger will dispense a known quantity of the drug or medication. Briefly described, the syringe 22 has a main body portion 24 in which a plunger portion 26 is engaged and can move relative thereto. The rear end of the main body portion 24 of the illustrated design has ears 27 thereon and the rear end of the plunger portion 26 has ears 28 thereon for engagement with the novel fluid pump device of the drug infusion system as described herein. A stopcock 30, which can be rotated between an open or closed position, is provided at an end of the syringe 22. In use, the stopcock 30 on the end of the syringe 20 is connected to conventional I.V. tubing (not shown) which is, in turn, connected to a needle (not shown). The needle is inserted into a patient, for example at the patient's arm, to which the drug or medication is to be delivered. The fluid feed device of the present invention can be easily attached to the patient so that the patient can be ambulatory.

To load the syringe 22 with medication, the stopcock 30 is rotated to an open position so that a passageway is provided into the main body portion 24 of the syringe 22. A predetermined quantity of medication or drug to be dispensed to the patient is drawn into the syringe 22 in a conventional manner by pulling back on the plunger portion 26 of the syringe 22 to draw medication through the stopcock 30 and into the main body portion 24. After the syringe 22 is loaded with the desired amount of medication, the stopcock 30 is rotated to the off or closed position. When the stopcock 30 is in the off or closed position, the plunger portion 26 cannot be depressed into the main body portion 24 and therefore, the medication cannot be accidentally or prematurely dispensed from the syringe 22. Once the syringe 22 is loaded with medication, the syringe 22 is ready to be engaged with the novel fluid pump device 120 of the present invention to dispense the medication or drug therefrom.

Figure 7:
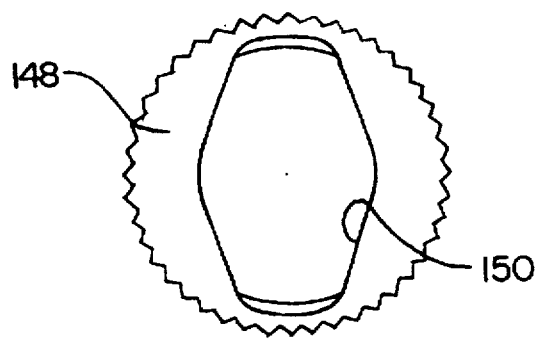
FIG. 7 is a front elevational view of the structure shown in FIG. 6.
Figure 8:
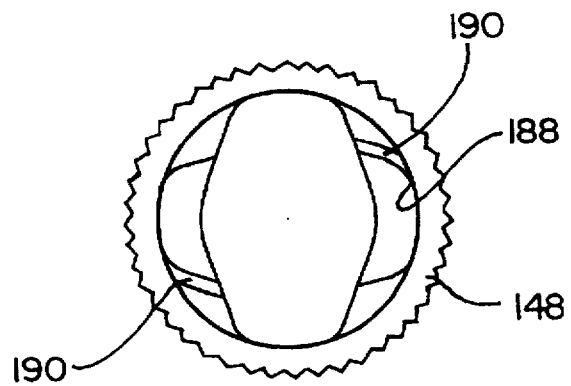
FIG. 8 is a cross-sectional view of the structure shown along line 8-8 in FIG. 6.

A first embodiment of the fluid pump or infusion device 120 of the drug infusion system is shown in FIGS. 1–5. An alternate structure for engaging the syringe 22 with the fluid pump device 120 of the present invention is shown in FIGS. 6–8. A second embodiment of the fluid pump or infusion device 220 of the drug infusion system is shown in FIGS. 9 and 10. A third embodiment of the fluid pump or infusion device 320 of the drug infusion system is shown in FIGS. 11–18, a fourth embodiment of the fluid pump or infusion device 420 is shown in FIGS. 19 and 20, and a fifth embodiment of the fluid pump or infusion device 520 is shown in FIGS. 21–23. Like elements in each embodiment are denoted with like reference numerals, with the first embodiment denoted by numerals in the one hundreds, with the second embodiment denoted by numerals in the two hundreds, with the third embodiment denoted by numerals in the three hundreds, with the fourth embodiment denoted by numerals in the four hundreds, and with the fifth embodiment denoted by numerals in the five hundreds.

Directing attention now to the first embodiment of the novel fluid pump device 120, shown in FIGS. 1–5, the device 120 generally includes a housing 121 which is formed from a cylinder member or portion 132 and a tube member 134 which are connected together. A front end of the cylinder 132 is attached to a rear end of the tube 134 by suitable means, such as adhesive or ultrasonic welding, to provide a unitary unit. The cylinder 132 and the tube 134 are made of suitable materials, such as plastic.

The tube 134 has a first or front end which is open and a second or rear end which is substantially closed by a rear wall member 136. The wall member 136 has a port or aperture 138 therethrough.

The cylinder 132 has a first or front end which is substantially closed by a front wall member 140. A port or aperture 142 is provided through the wall member 140. A second or rear end of the cylinder 132 has a cap or plug 144 which is attached thereto by suitable means, such as adhesive or the like, to completely close the end of the cylinder 132. The cap or plug 144 is made of suitable materials, such as plastic. The aperture 142 in the front wall of the cylinder 132 is approximately the same diameter as the aperture 138 in the rear wall member 136 of the tube 134 and the apertures 138, 142 are aligned with each other.

At the front end of the tube 134, a sleeve member 146 is attached thereto by suitable means, such as adhesive, and encircles the front end of the tube 134. A cylindrical locking cap 148 is attached to the sleeve member 146. The locking cap 148 has an aperture 150 therethrough which provides an entranceway for the end of the plunger portion 26 of the syringe 22 therethrough so that the syringe 22 can be engaged within the fluid pump device 120 and which prevents or deters detachment of the plunger portion 26 therefrom as described herein. The aperture 150, as best shown in FIG. 1, has a conforming lobular shape to that of the ears 27 on the rear end of the main body portion 24 of the syringe 22. As such the ears 27 may be engaged in the lobes of aperture 150, and the body of the syringe rotated to dispose the ears 27 between the ends of locking cap 148 and sleeve member 146, as shown in FIGS. 4 and 5.

Housed within the tube 134 of the fluid feed device 120 is a drive component or rod cap 152 against which the end of the plunger portion 26 engages when the syringe 22 is disposed within the fluid feed device 120. The drive component 152 is in the form of a piston member. An elongate rod 154 is securely connected to and extends from the drive component 152 through the aligned apertures 138, 142 in the rear wall 136 of the tube 134 and the front wall 140 of the cylinder 132, respectively. The opposite end of the elongate rod 154 is engaged with a second piston member 156 which is housed in the cylinder 132. The apertures 138, 142 are slightly larger than the diameter of the rod 154 so that the rod 154 has sufficient clearance from the wall members 136, 140 such that the rod 154 can move relative to the housing 121 for reasons described herein.

A biasing member in the form of a spring 158 of known spring force is engaged between the rear wall member 136 of the tube 134 and the drive component 152 for reasons described herein. A first end of the spring 158 is securely attached to the drive component 152 by a grip ring or the like and a second end of the spring 158 is securely attached to the rear wall member 136 of the tube 134 by suitable means, such that the spring 158 will tend to bias the drive component or piston 152 to the left as viewed in FIG. 2.

The movable piston member 156 connected to the rear end of the rod 154, FIGS. 2 and 3, divides the cylinder 132 into a first chamber 162 and a second chamber 164. The first chamber 162 is defined by the area of the cylinder 132 between the piston member 156 and the cap or end wall 144 and the second chamber 164 is defined by the area of the cylinder 132 between the piston member 156 and the front wall 140 of the cylinder 132.

A fluid medium 166 of known characteristics completely fills both the first chamber 162 and the second chamber 164. The fluid medium 166 is preferably mineral oil or Dow medical silicone fluid. Both of these fluids have good stability throughout a wide temperature range.

To prevent the flow of fluid medium 166 from the cylinder 132 and into the tube 134, an 0-ring 168 is provided around the rod 154, FIG. 3, and is seated in the aperture 138 in the rear wall 136 of the tube 134.

To allow communication of the fluid medium 166 between chambers 162 and 164, a valve structure designated generally 170, is provided, as best shown in FIG. 3. The valve structure 170 provides for rapid flow or movement of the fluid medium 166 from chamber 162 into chamber 164, when the infusion device 120 is cocked. As will be explained, cocking of the device 120 occurs when the plunger 26 is engaged within tube 134 to move the drive component 152, rod 154 and piston 156 to the right as viewed in FIGS. 2 & 3. This movement will also compress spring 158. Movement of fluid from chamber 162 to chamber 164 after the unit has been cocked, is controlled by a metering orifice in the form of a tube, as discussed more fully hereafter. The valve structure 170 a passageway 172 through the piston member 156 and a plate member 174 which is biased against the piston member 156 by a spring 176 so as to abut against the piston member 156 to prevent the flow of fluid medium 166 through the passageway 172 and is capable of being biased away from the piston member 156 and passageway 172 by fluid pressure so that fluid medium 166 can pass through the passageway 172 from the first chamber 162 to the second chamber 164. The plate member 174 is biased against the piston member 156 by a valve spring 176 which has one end attached to the rod 154 at a predetermined distance away from the plate member 174 and a second end which is attached to the plate member 174. The valve spring 176 is of a known spring force.

The plate member 174 has an aperture 175 therethrough and the piston member 156 has an aperture 177 therethrough which is aligned with the aperture 175 in the plate member 174. A metering orifice in the form of a tube 178 is engaged or seated in aperture 177 and extends through the aligned aperture 175 in the plate member 174. The metering orifice is an elongate tube 178 having an axial passageway therethrough so that the fluid medium 166 can be passed therethrough from the second chamber 164 through the plate member 174 and the piston member 156 and into the first chamber 162 as described hereinafter. The metering tube 178 is made of suitable materials, such as stainless steel, and is of a predetermined length and diameter so that the passage rate of fluid medium 166 from the second chamber 164 to the first chamber 162 can be precisely controlled.

To prevent the passage of fluid medium 166 from between the inner wall of the cylinder 132 and the piston member 156, a plurality of O-rings 180 are provided, which are capped by the piston member 156 and engage the inner wall of the cylinder 132 so that the piston member 156 can move relative to the cylinder 132 while confining the passage of fluid medium 166 between the chambers 162, 164 to the metering orifice 178 and aperture 172 and preventing flow of fluid around the edges of the piston member 156. A rubber gasket 182 can be provided between the plate member 174 and the piston member 156 to prevent or minimize leakage of the fluid medium 166 from the first chamber 162 to the second chamber 164 when the plate member 174 is seated against the piston member 156.

Now that the specifics of the structure and components of the first embodiment of the fluid feed device 120 have been described, a description of how the system operates to dispense a controlled, predetermined amount of liquid medication or drug from the syringe 22 will be detailed. Initially, as shown in FIG. 2, the fluid feed device 120 is in a fully extended or expended position with the drive component 152 in its far left position, as viewed, generally abutting against the inside of the locking cap 148. The spring 158 and the valve spring 176 are uncompressed. Since the valve spring 176 is not compressed, the plate member 174 is seated against the piston member 156 so that there is no passage of fluid medium 166 between the first and second chambers 162, 164 in the cylinder 132.

Thereafter, the syringe 22 with stopcock 30 closed, which has been loaded with medication, is engaged with the device 120 by inserting the end of the plunger portion 26 through the aperture 150 in the locking cap 148 until the end of the plunger portion 26 abuts against the drive component 152. The ears 28 of the plunger portion 26 engage with the drive component 152.

To load the syringe 22 within the device 120, the syringe 22 is pushed into the tube 134 such that the plunger portion 26 enters into the tube 134. The tube 134 provides a compartment in which the plunger portion 26 is received. The drug or medication within the syringe 22 is not dispensed from the syringe 22 when the syringe 22 is pushed into the device 120 since the closed stopcock 30 prevents the plunger portion 26 from being depressed into the main body portion 24.

As the plunger portion 26 moves into the tube 124, the drive component 152 is pushed backwardly or to the right, as viewed, into the tube 134 which causes the rod 154 to move backwardly into the tube 134 and the spring 158 to compress between the drive component 152 and the rear wall 136 of the tube 134. As the rod 154 moves backwardly, this causes the piston member 156 to move backwardly and pressurize the liquid medium 166 behind the piston member 156. The plate member 174 is unseated from engagement against the piston member 156 due to the pressure of the fluid medium 166 acting on the plate member 174 through the passageway 172. This action overcomes the force of the valve spring 176 which compresses to unseat plate 174 from passageway 172. Since the plate member 174 is not seated against the piston member 156, the fluid medium 166 flows from the first chamber 162 through the passageway 172 and into the second chamber 164. Some fluid medium 166 will also flow through the metering orifice provided by tube 178 and into the second chamber 164, but the primary source of fluid movement between said chambers is the passageway 172. The plunger portion 26 of the syringe 22 can be rapidly depressed into the device 20 since the passageway 172 allows a large quantity of fluid medium 166 to rapidly pass from the first chamber 162 to the second chamber 164.

Once the syringe 22 has been fully inserted into the device 20, the syringe 22 is twisted so that the ears 27 on the end of the main body portion 24 rotate within the rod cap 148 so that the ears 27 are engaged between the rod cap 148 and the sleeve 146 to prevent the syringe 22 from being accidentally dislodged from the device 120. As shown in FIG. 4, once the syringe 22 has been completely inserted into the tube 134, the device 120 is fully cocked and the spring 158 is in a compressed state. The spring 158 cannot expand since the plunger portion 26 of the syringe 22 cannot depress into the main body portion 24 until the stopcock 30 is rotated to the open position. Once backward or retractive movement of the piston member 156 is stopped, pressure from the fluid medium 166 is no longer being applied to the plate member 174 which allows the valve spring 176 to expand which biases the plate member 174 against the piston member 156. Thus, fluid medium 166 cannot pass through the aperture 172 in the piston member 156.

Once it is desired to dispense the medication or drug from the syringe 22, the stopcock 30 is rotated to the open position as shown by the arrow in FIG. 4. The plunger 26 is now free to be depressed into the main body portion 24. The spring 158 expands which causes the drive component 152 to move forwardly in the tube 134 which forces the plunger portion 26 into the main body portion 24 of the syringe 22 thereby dispensing the medication or drug from the syringe 22. This action places a positive pressure on the syringe 22 to dispense the medication or drug from therewithin.

As the spring 156 expands, as shown in FIG. 5, the rod 154 translates forwardly in the housing 121 which causes the piston member 156 to move forwardly relative to the cylinder 132 and pressurize the fluid medium 166 forward of the piston member 156. Since the passageway 172 is sealed by plate member 174, fluid medium 166 can pass from the second chamber 164 to the first chamber 162 only through the metering orifice provided by the tube 178. Fluid medium 166 cannot pass through the passageway 172 in the piston member 156 since the passageway 172 is sealed by the plate member 174 which is biased against the piston member 156 by the valve spring 176. In addition, pressure is applied to the front side of the plate member 174 by the fluid medium 166 which ensures that the plate member 174 remains seated against the piston member 156.

The rod 154 provides an operative connection between the piston member 156 and the drive component 152, such that the rate of movement of the piston member 156 through the fluid medium 166 controls the rate of movement of the drive component 152, and correspondingly to the rate of movement of the syringe plunger 26. As can be appreciated, the viscosity of fluid medium 166, spring 158 and the size of the metering orifice provided by the tube 178 control the rate of movement of piston 156, and as such the delivery rate of the medication from syringe 22. In this first embodiment of the device 120, there is a one-for-one movement of the fluid medium 166 from the first chamber 162 to the second chamber 164 since the chambers are of equal diameter.

Once the medication or drug is fully dispensed from the syringe 22, the plunger portion 26 is completely depressed into the main body portion 24. The device 120 will have returned to its initial position as described hereinabove and as shown in FIG. 2.

Attention is now directed to the alternate mounting structure for the syringe 22, shown in FIGS. 6–8, by which the syringe 22 can be engaged with the fluid feed device 120 so that the syringe 22 is prevented from becoming dislodged from the device 120 during delivery of the medication or drug to the patient. This modified design also takes up any "play" or lost motion in the system so that once the unit is cocked and the stopcock released, medication will flow immediately. In this structure, the sleeve member 146 has been eliminated. The front end of the tube 134 has threads 184 on its outer surface and the inner surface of the locking cap 148 has mating threads 186 thereon. The aperture 150 in the locking cap 148 corresponds in shape to the ears 27 on the main body portion 24 of the syringe as shown in FIG. 7. The locking cap 148 has pockets 188 and lugs or stops 190 therein for reasons described herein. The pockets 188 correspond in shape to the ears 27 on the end of the main body portion 24 of the syringe 22 and are perpendicular to the lobes of the aperture 150.

To engage the syringe 22 with the device 120, the end of the plunger portion 26 is inserted into the tube 134 and engaged with the drive component 152. The device 120 is moved to a fully cocked position as described hereinabove. The syringe 22 is rotated ninety degrees clockwise until the ears 27 of the main body portion 24 move into the pockets 188 and the ears 27 abut against the lugs 190. If the syringe 22 is rotated further than ninety degrees, this rotation starts to screw the locking cap 148 on tighter around the tube 134 due to the thread engagement. Finally, the locking cap 148 is grasped and the syringe 22 is rotated clockwise relative to the locking cap 148 to cause the ears 27 of the main body portion 24 to abut tightly against the lugs 190 within the pockets 188. This structure causes the plunger portion 26 to securely abut against the drive component 152 to prevent any dead space between the elements. It is to be understood that this structure can be used with any of the embodiments of the fluid feed device disclosed herein and is not limited to the first embodiment. Also, in place of the screw threads 184; 186, a camming arrangement or similar structure could be employed.

Now turning to the second embodiment of fluid feed or infusion device 220 of the drug infusion system, as shown in FIGS. 9 and 10, the device 220 includes a housing 221 formed from a tube 234. A cylinder 232 is positioned within the tube 234. The tube 234 and the cylinder 232 are formed from suitable materials, such as plastic. A second or rear end of the cylinder 232 is attached to a second or rear end of the tube 234 by a flange 292.

A first or front end of the tube 234 has a locking cap 248 attached thereto by suitable means, such as adhesive. In this embodiment, the sleeve 146 has been eliminated, however, it will be appreciated that it may be included in the design if desired. A second or rear end of the tube 234 is completely closed by a cap 244 which also closed the second or rear end of the cylinder 232. The first or front end of the cylinder 232 has a front wall 240 which has an aperture 242 therethrough.

Housed within the tube 234 of the fluid feed device 220 is a drive component or a rod cap 252 which the end of the plunger portion 26 engages when the syringe 22 is engaged with the fluid feed device 220. An elongate rod 254 is securely connected to and extends from the drive component 252 through the aperture 242 in the front wall 240 of the cylinder 232 to a piston member 256 which is housed in the cylinder 232. The aperture 242 is slightly larger than the diameter of the rod 254 so that the rod 254 has sufficient clearance from the wall member 240 so that the rod 254 can move relative to the housing 221 for reasons described herein.

A spring member 258 of known spring force is engaged between the flange 292 which is proximate to the cap 244 and the drive component 252. A first end of the spring 258 is securely attached to the drive component 252 and a second end of the spring 258 is securely attached to the flange 292 by suitable means.

The piston member 256 connected to the rear end of the rod 254 divides the cylinder 232 into a first chamber 262 and a second chamber 264. The cylinder 232 further includes a wall 201 which is spaced a predetermined distance away from the front wall 240 and lies between the front wall 240 and the piston member 256. A plate 203 abuts against the wall 201.

The area between the piston member 256 and the locking cap 244 defines the first chamber 262. The area between the piston member 256 and the wall 201 defines the second chamber. The area between the wall 201 and the front wall 240 of the cylinder 232 defines a transfer chamber 205. A return orifice which takes the form of a tube 209 interconnects the transfer chamber 205 and the first chamber 262. The wall 201 and the plate 203 have aligned apertures through which the rod 254 passes. The ends of the plate 203 are secured to the inner walls of the cylinder 232 so that the plate 203 cannot move relative to the cylinder 232.

A fluid medium 266 of known characteristics, such as discussed above with respect to the first embodiment, completely fills the first chamber 262, the second chamber 264, the transfer chamber 205 and the return tube 209. To prevent the flow of fluid medium 266 from the cylinder 232 into the tube 234, an O-ring 268 is provided around the rod 254 and is seated in the aperture 242 in the front wall 240 of the cylinder 232. To prevent the passage of fluid medium 266 from between the inner wall of the cylinder 232 and the piston member 256, an 0-ring 280 is provided between the piston member 256 and the inner wall of the cylinder 232 so that the piston member 156 can move relative to the cylinder 232 while preventing passage of fluid medium 266 between the chambers 262, 264 around the edges of the piston member 256. To prevent the flow of fluid medium 266 from the second chamber 264 through the aperture in the wall 201 to the transfer chamber 205, an 0-ring 207 is seated within the opening in the wall 201. To allow communication of the fluid medium 266 from the first chamber 262 to the transfer chamber 205, the return orifice which takes the form of the elongate return tube 209 is connected between the chambers 262, 205 and is used as described herein.

To allow communication of the fluid medium 266 from the transfer chamber 205 to the second chamber 264, as is required when the device is to be cocked to the ready condition, a valve structure 270 is provided, as best shown in FIG. 7. The valve structure 270 includes a passageway 272 through the plate 203 and the wall 201 and includes a J-shaped pull ring 211 which biases a valve 274 into the passageway 272. A thumb grip 213 is provided so that a medic can easily grasp the device 220 and pull onthe pull ring 211 which can be pulled with the index finger.

The pull ring 211 extends from the rear end of the device 220 along the outside of the cylinder 232 and inside the tube 234 and through the front wall 240 of the cylinder 232 and into the transfer chamber 205. The end of the J-shaped pull ring 211 is attached to the valve 274 and is used to bias the valve 274 into an unseated position from the passageway 272 through the plate 203 and the wall 201 to allow the rapid flow of fluid medium 266 through the passageway 272. The pull ring 211 can be released to allow the valve 274 to reseat in the passageway 272 to prevent the flow of fluid medium 266 through the passageway 272 from the transfer chamber 205 to the second chamber 264. It is to be understood that other types of manually actuated valves could be used in this embodiment other than the pull ring assembly disclosed and described herein.

The passageway 272 and the valve 274 have corresponding tapered shapes which mate with each other when the valve 274 is seated in the passageway 272. The tapered shape helps to guide the valve 274 into the passageway 272 when it is being seated in the passageway 272. To prevent the flow of fluid medium 266 from the second chamber 264 into the transfer chamber 205 through the passageway 272 in which the valve 274 is seated, an 0-ring 282 is provided around the valve 274 and is seated in the aperture through the wall 201.

The valve 274 is biased into the passageway 272 by a valve spring 276 which has one end attached to the front side of the front wall 240 of the cylinder 232 and a second end which is attached to the pull ring 211. The valve spring 276 is of a known spring force.

A metering orifice provided by tube or passageway 278 is housed or formed within the stem portion of the valve 274 and has a first portion which is aligned with the length of the valve 274 and a second portion which is perpendicular to the first portion so that an open passageway or port opening is provided into the transfer chamber 205. Thus a path is provided by the metering orifice 278 between the second chamber 264 and the transfer chamber 205. The metering orifice is an elongate tube 278 having a passageway therethrough. The metering tube 278 is of a predetermined length and diameter so that the passage rate of fluid medium 266 from the second chamber 264 to the transfer chamber 205 and thus, the first chamber 262, can be precisely controlled.

Now that the specifics of the structural feature of the second embodiment of the fluid feed or infusion device 220 have been described, a description of how the system dispenses a medication or drug from the syringe 22 is described. Initially, as shown in FIG. 9, the fluid feed device 220 is in a fully extended position with the drive component 252 generally abutting against the inside of the locking cap 248. The spring 258 and the valve spring 276 are expanded. Since the valve spring 276 is not compressed, the valve 274 is seated within the passageway 272 so that there is no passage of fluid medium 266 between the chambers 262, 264 and 205 in the cylinder 232.

Thereafter, the syringe 22, which has been loaded with medication, is engaged with the device 220 as described hereinabove. To load the syringe 22 within the device 220, the pull ring 211 is pulled to unseat the valve 274 from the passageway 272. As the valve 274 is unseated, the O-rings 282 slides out from its engagement with the plate 203 and out of the passageway 272 so that fluid medium 266 can flow rapidly through the passageway 272. The valve spring 276 is compressed when the pull ring 211 is pulled. Thereafter, the syringe 22 is pushed into the tube 234 such that the plunger portion 26 enters into the tube 234. The tube 234 provides a compartment in which the plunger portion 26 is received.

As the plunger portion 26 moves into the tube 234, the drive component 252 is pushed rearwardly into the tube 234 which causes the rod 254 to move rearwardly into the tube 234 and the spring 258 to compress between the drive component 252 and the flange 292. As the rod 254 moves rearwardly, the piston 256 moves rearwardly which pressurizes the fluid medium 266 and forces the fluid medium 266 through the return tube 209 and into the transfer chamber 205. Since the valve 274 is not seated within the passageway 272, the fluid medium 266 freely flows from the transfer chamber 205 through the passageway 272 and into the second chamber 264. Some fluid medium will flow through the metering orifice 278 and into the second chamber 264. The plunger portion 26 of the syringe 22 can be rapidly depressed into the device 20 since the passageway 272 allows a large quantity of fluid medium 266 to rapidly pass from the transfer chamber 205 to the second chamber 264 in a short period of time.

Once the syringe 22 has been fully inserted into the device 20, the syringe 22 is securely engaged with the device 220 as described hereinabove. Once the syringe 22 has been completely inserted into the tube 234, the device 220 is fully cocked and the spring 258 is in a fully compressed state. Thereafter, the pull ring 211 is released and the valve spring 276 is allowed to expand which causes the valve 274 to reseat within the passageway 272. The O-rings 282 slides or rolls along the length of the valve 274 until it is reseated in the passageway 272. The O-rings 282 cannot roll off of the valve 274 because the valve 274 has an enlarged head portion 213 which prevents the O-rings 282 from detaching from the valve 272. The tapered passageway 272 aids in reseating the O-rings 282 in its proper place by forcing the O-rings 282 to move along the length of the valve 272 so that the valve can fully reseat within the passageway 272.

Once it is desired to dispense the medication or drug from the syringe 22, the stopcock 30 is rotated to the open position. The plunger portion 26 is now free to be depressed into the main body portion 24. The spring 258 expands which causes the drive component 252 to move forwardly in the tube 234 which forces the plunger portion 26 into the main body portion 24 of the syringe 22 thereby dispensing the medication or drug from the syringe 22. This action places a positive pressure on the syringe 22 to dispense the drug from therewithin.

As the spring 258 expands, the rod 254 translates forwardly in the housing 221. Fluid medium 266 is forced from the second chamber 262 through the metering orifice provided by tube 278 into the transfer chamber 205 and fluid 266 from the transfer chamber 205 can be returned to the first chamber 262 via return orifice provided by tube 209. Fluid medium 266 cannot pass through the passageway 272 since it is sealed by the valve 274. The fluid medium 266 is, therefore, forced to move through the metering tube 278 with the size and length of the tube 278 controlling and determining the rate of movement of piston 256 and correspondingly, drive component 252.

Thus, the rod 254 provides an operative connection between the fluid medium 266 and the syringe 22. In this second embodiment of the device 220, there is approximately one-for-one movement of the fluid medium 266 from the first chamber 262 to the second chamber 264 since the chambers are of equal diameter.

Once the medication or drug is fully dispensed from the syringe 22, the plunger portion 26 is completely depressed into the main body portion 24. The device 220 returns to its initial position as described hereinabove and as shown in FIG. 9.

Attention is now directed to the third embodiment of the fluid feed or infusion device 320, as shown in FIGS. 11-18. The rod member 154, 254 used in the first and second embodiments of the device to interconnect the piston 156; 256 with the drive component 154; 254 has been eliminated in this embodiment. Instead, the fluid medium 366 acts directly upon the drive member or rod cap 352.

The novel fluid feed device 320 generally includes a housing 321 which is formed from a cylinder 332 which defines a first chamber 362 and a tube 334 which defines a second chamber 364 and which are connected together by a transfer chamber 305 which houses a valve structure 370 to allow selective communication of a fluid medium which is housed within the chambers 362, 364 and 305. A front end of the tube 334 is attached to a rear end of the transfer chamber 305 and a rear end of the cylinder 332 is attached to the front end of the transfer chamber 305 by suitable means, such as adhesive or the like, to provide an unitary construction. The cylinder 332, tube 334 and transfer chamber 305 are made of suitable materials, such as plastic.

The cylinder 332 has a first or front end which is open and a second or rear end which is substantially closed by the wall 336 of the transfer chamber 305. The wall member 336 has a port or aperture 338 therethrough.

The cylinder 332 has a first or front end which is substantially closed by the wall 340 of the transfer chamber 305. A port or aperture 342 is provided through the wall member 340. A second or rear end of the tube 334 has a cap 344 which is attached thereto by suitable means, such as adhesive, to completely close the end of the tube 334. The cap 344 is made of suitable materials, such as plastic. The aperture 342 has a one-way flapper or umbrella valve 315 therethrough to only allow the passage of fluid from the transfer chamber 305 into the second chamber 364 but not in the opposite direction.

At the front end of the cylinder 332, a cylindrical locking cap 348 is attached thereto by suitable means, such as adhesive, and encircles the front end of the cylinder 332. The locking cap 348 has an aperture therethrough which provides an entranceway for the end of the plunger portion 26 of the syringe 22 therethrough so that the syringe 22 can be engaged within the fluid feed device 320.

Housed within the cylinder 332 of the fluid feed device 320 is a drive component or a rod cap 352, which in this embodiment is in the form of a second piston member, and against which the end of the plunger portion 26 engages when the syringe 22 is engaged with the fluid feed device 20. The first chamber 362 is defined between the drive component 352 and the wall 336 of the transfer chamber 305.

A piston member 356 is housed in the tube 334. The second chamber 364 is defined between the piston member 356 and the rear wall 340 of the transfer chamber 305. A spring 358 of known spring force is securely engaged between the cap 344 of the tube 334 and the piston member 356 by suitable means and for reasons described herein.

A fluid medium 366 of known characteristics, and similar to the medium discussed with regard to the previous embodiments, completely fills chamber 305 and the portion of chamber 362 to the right of the drive component 352, as viewed, and to the left of the piston member 356. Thus, the fluid medium 366 extends from the drive component 352, through the transfer chamber 305 and into chamber 364 up to the face of piston 356. The opposite side of piston 356 wherein the spring 358 is housed is fluid free. To prevent the flow of fluid medium 366 from the first chamber 362 around the drive component 352 and out of the cylinder 332 and from the second chamber 364 around the piston member 356 and into the spring compartment in the tube 334, a plurality of O-rings 317 are provided around each of the drive component 352 and around the piston member 356. As can be appreciated with this arrangement the drive component 352 is also a piston.

The valve structure 370 housed within the transfer chamber 305 allows selective communication of fluid medium 366 from the first chamber 362 to the second chamber 364 through the transfer chamber 305. The valve structure 370 includes a piston or valve plunger 319 which is biased by a spring 321 and can be moved from a first position, which allows communication of fluid medium 366 through the port 338 and into the transfer chamber 305 and through the one-way valve 315 and into the second chamber 364, and into a second position, which blocks the aperture 338 so as to prevent fluid flow in this manner through the transfer chamber.

The piston or valve plunger 319 includes a platform 323 which is connected by a rod 325 to a thumb engaging portion 327 which protrudes outwardly from the side wall of the transfer chamber 305. A spring 321 is sandwiched between the platform 323 and the opposite side of the transfer chamber 305 to bias the plunger 319 to the valve-closed position of FIGS. 14 and 15. The piston plunger 319 is sealed by a plurality of O-rings 329, 331, 333, which seal the transfer chamber. The O-rings 331 is seated against the platform 323 to prevent the flow of fluid medium 366 past the platform 323. The O-rings 333 prevents fluid medium from leaking out of the transfer chamber 305 through the aperture in which the portion 327 is seated. The O-rings 329 prevents the fluid medium 366 from flowing into the compartment where the spring 321 is housed.

Figure 16:
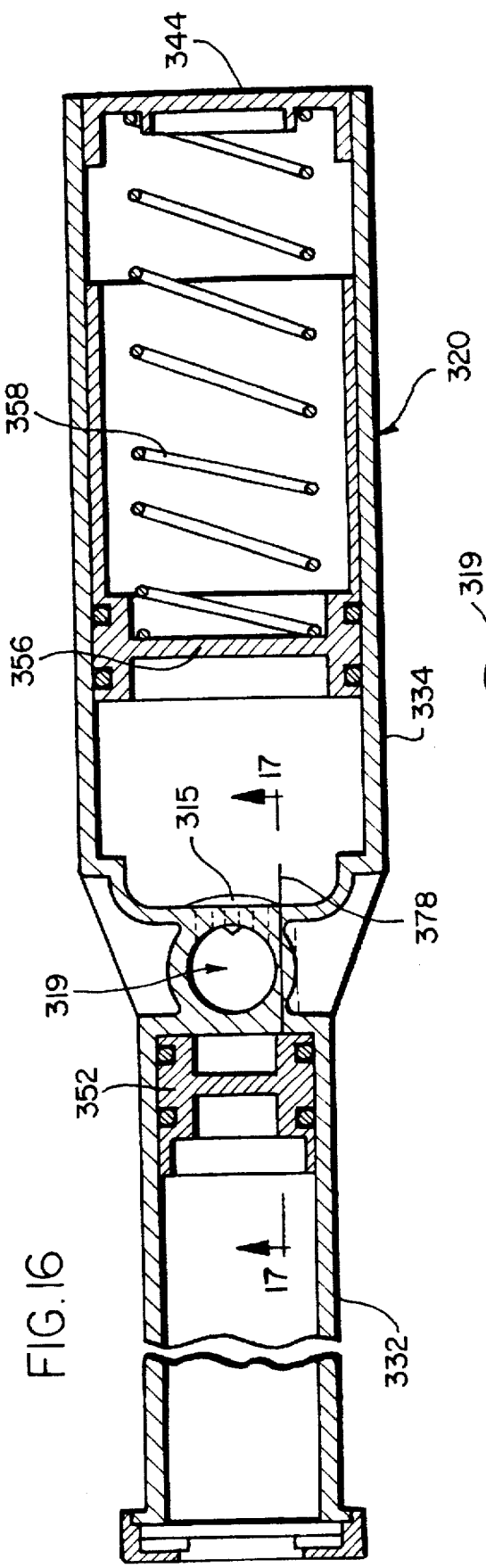
FIG. 16 is a horizontal cross-sectional view (i.e. taken at a right angle to FIG. 14) of the third embodiment of the fluid infusion device without a syringe engaged therewith but in a fully cocked position.
Figure 17:
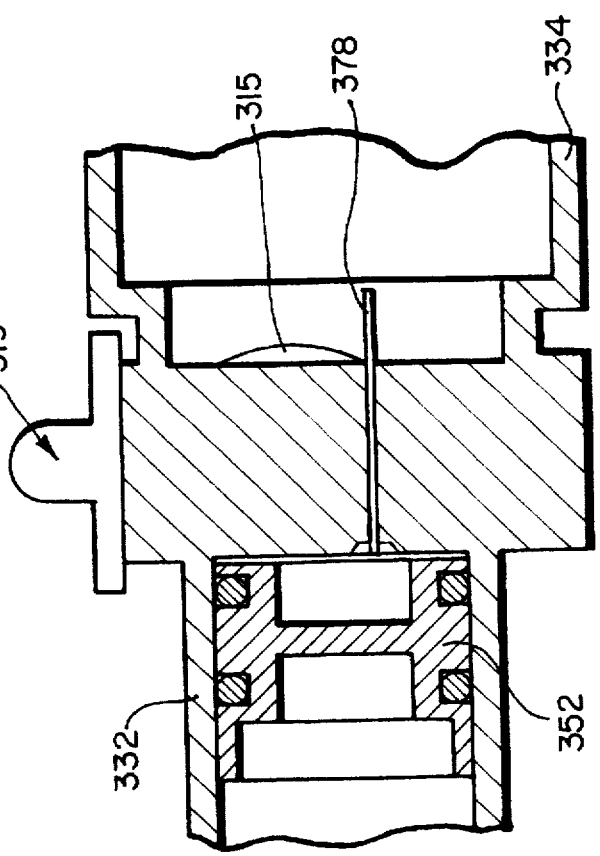
FIG. 17 is a cross-sectional view of the third embodiment of the fluid infusion device along line 17—17 of FIG. 16.

The walls 336, 340 of the transfer chamber 305 have aligned apertures therethrough through which a metering tube 378, like that of the previous embodiments, is seated to provide the desired metering orifice. The metering tube 378 is an elongate tube having an axial passageway therethrough so that fluid medium 366 can be passed from the second chamber 364 into the first chamber 362 as described herein while bypassing the transfer chamber 305, see FIGS. 16 and 17. The metering tube 378 is offset from the piston plunger 319 as shown in FIGS. 16 and 17. Thus, the metering orifice which is provided by tube 378 is never blocked by the piston plunger 319 as it bypasses the transfer chamber 305.

Now that the specifics of the third embodiment of the fluid feed or infusion device 320 have been described, a description of how the system dispenses a medication or drug from the syringe 22 is described. Initially, as shown in FIG. 18, the fluid feed device 320 is in a fully extended position with the drive component 352 generally abutting against the inside of the locking cap 348. The spring 358 is expanded. Prior to depression of the valve plunger 319 into the transfer chamber, the spring 321 is not compressed and the piston or valve plunger 319 is in the valve-closed position of FIG. 15. After the piston or valve plunger 319 is depressed, as shown in FIG. 12, the spring 321 is compressed and the platform 323 is moved to a position which is clear from the aperture 338 so that fluid medium 366 can flow into the transfer chamber 305. The O-rings 333 is moved to a position which is above the aperture 342 and the O-rings 331 is moved to a position which is below the port 338 as shown FIG. 13.

Thereafter, the syringe 22, which has been loaded with medication, is engaged with the device 320 as described hereinabove. The syringe 22 is pushed into the cylinder 332 such that the plunger portion 26 enters into the cylinder 332. The cylinder 332 provides a compartment in which the plunger portion 26 is received.

As the plunger portion 26 is moved into the cylinder 332, the drive component 352 is pushed rearwardly which applies pressure to the fluid medium 366 housed within the first chamber 352 and causes the fluid medium 366 to move through the port 338 and into the transfer chamber 305. Some fluid medium 366 will flow through the metering orifice provided by tube 378 and into the second chamber 364.

After the fluid medium 366 has passed into the transfer chamber 305, the fluid medium 366 then passes through the aperture 342 over which the umbrella valve 315 is seated. The pressure on the underside of the umbrella valve 315 causes it to unseat or open and to allow fluid medium 366 to move rapidly through the aperture 342 and into the second chamber 364. As the fluid medium 366 passes into the second chamber 364, the pressure from the fluid medium 366 drives the piston member 356 backwardly which causes the spring 358 to compress between the piston member 356 and the cap or end wall 344. The plunger portion 26 can be rapidly depressed into the device 320 since a large quantity of fluid medium 366 can rapidly pass from the first chamber 362 through the transfer chamber 305 and into the second chamber 364.

Figure 15:
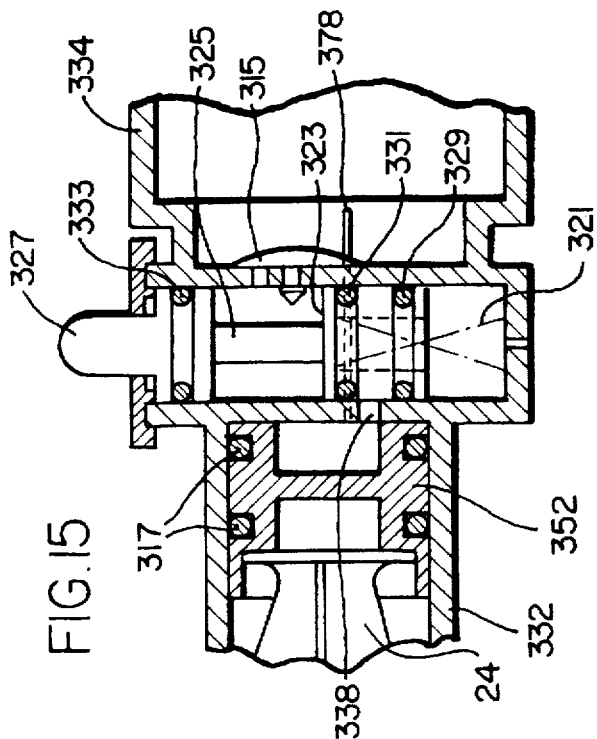
FIG. 15 is an enlarged cross-sectional view of the portion of the third embodiment of the fluid infusion device shown in the circle in FIG. 14.
Figure 13:
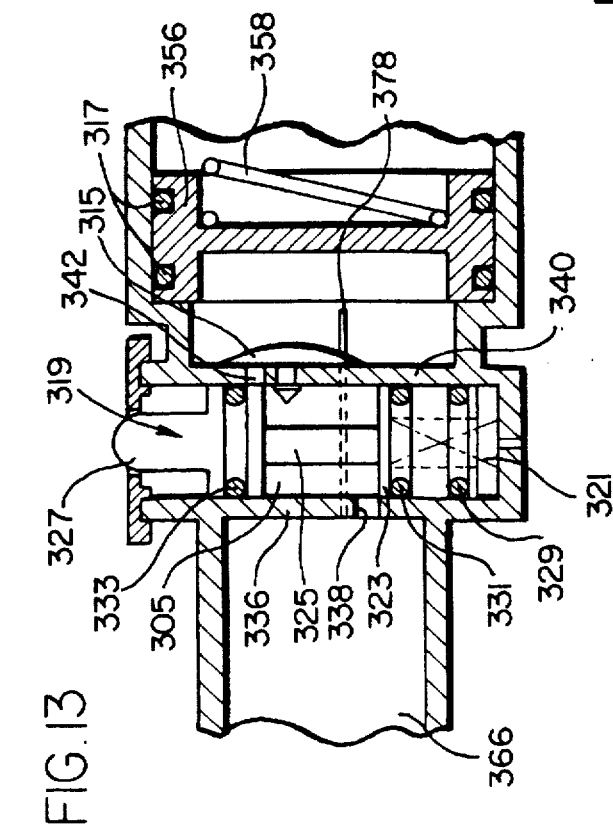
FIG. 13 is an enlarged cross-sectional view of the portion of the third embodiment of the fluid infusion device shown in the circle in FIG. 12.
Figure 14:
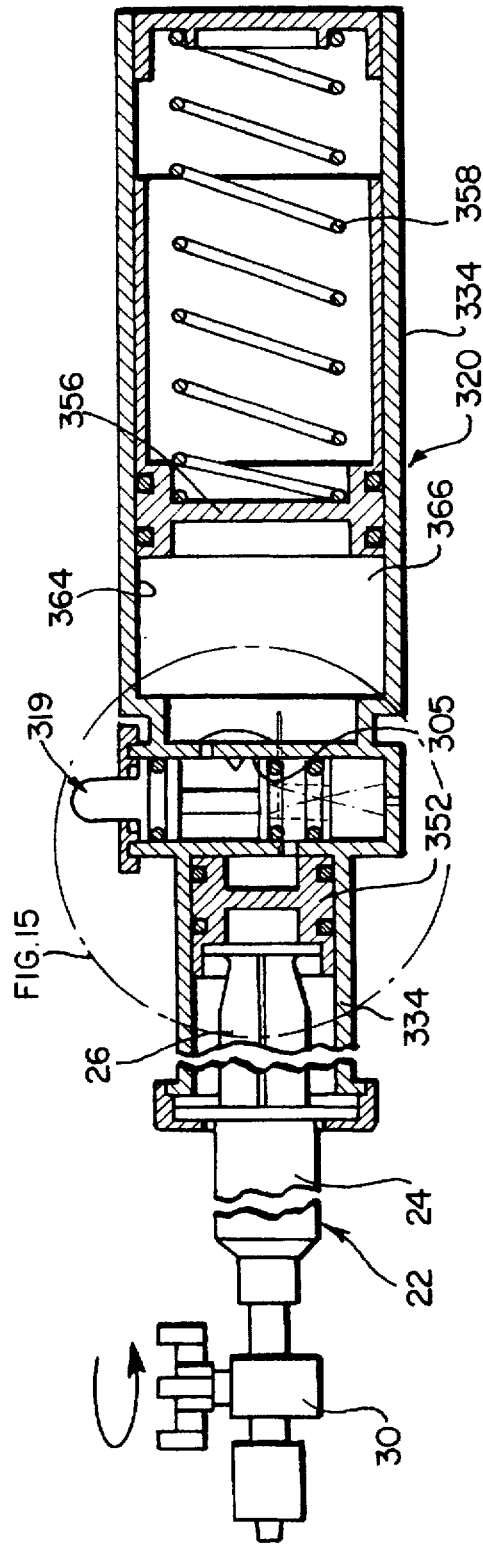
FIG. 14 is a vertical cross-sectional view of the third embodiment of the fluid infusion device with a syringe engaged therewith and in a fully cocked or ready position.

Once the syringe 22 has been fully inserted into the device 320, the syringe 22 is engaged with the device 320 as described hereinabove. As shown in FIG. 13, once the syringe 22 has been completely depressed into the cylinder 332, the device 320 is fully cocked and the spring 358 is in a fully compressed state. Once rearward movement of the drive component 352 is stopped, pressure from the fluid medium 366 is no longer being applied to the umbrella valve 315 and the valve 315 closes to prevent the passage of fluid medium 366 from chamber 364 into the transfer chamber 305. Therefore, the piston plunger 319 is released thereby allowing the spring 321 to expand, as shown in FIGS. 14 and 15. The platform 323 is driven back into its initial state. The O-rings 331 is returned to its position between the port 338 and the aperture 342. Thus, fluid medium 366 cannot flow through the transfer chamber 305 by way of the apertures 338 and 342.

Once it is desired to dispense the medication or drug from the syringe 22, the stopcock 30 is rotated to the open position and the plunger portion 26 is now free to be depressed into the main body portion 24. The spring 358 expands which causes the piston member 356 to move forwardly in the tube 334 which pressurizes and forces the fluid medium in the second chamber 364 through the metering orifice provided by tube 378 and into the first chamber 362. The metering tube 378 is not blocked by the release of the piston plunger 319 since it is offset from the plunger 319, and in effect, bypasses the transfer chamber 305, as shown in FIGS. 16 and 17. The fluid medium 366 cannot flow through the one-way umbrella valve 315 since it is sealed against the wall 340 of the transfer chamber 305. In addition, pressure is applied to the umbrella valve 315 by the fluid medium 366 which ensures that the valve 315 remains sealed against the wall 340. The fluid medium 366 flows into the first chamber 362 through the metering orifice provided by tube 378 and acts upon and forces the drive component 352 to the left as viewed, which depresses the plunger portion 26 into the main body portion 24 of the syringe 22 thereby dispensing the medication or drug from the syringe 22. This action places a positive pressure on the syringe 22 to dispense the drug from therewithin.

In this third embodiment of the device 320, the movement between chambers is greater than one to one since the cylinder 332 is smaller than the tube 334. It is to be understood, however, that a one for one ratio could be achieved if desired by making the chambers the same diameter.

Once the medication or drug is fully dispensed from the syringe 22, the plunger portion 26 is completely depressed into the main body portion 24. The device 320 returns to its initial position as described hereinabove.

Directing attention now to the fourth and fifth embodiments of the novel drug infusion system of the present invention, it will be appreciated that these embodiments show a fluid feed or infusion device 420, 520 which is similar to the fluid feed device 320 of the third embodiment. The fourth embodiment of the fluid feed device 420 is shown in FIGS. 19 and 20 and the fifth embodiment of the fluid feed or infusion device 520 is shown in FIGS. 21 and 22. These fluid feed devices 420, 520 are similar to that of the third embodiment in that the fluid medium 466, 566 acts directly upon the drive member or rod cap 452, 552, respectively.

Each novel fluid feed or infusion device 420, 520 generally includes a housing 421, 521 which is formed from a cylinder 432, 532 which defines a first chamber 462, 562 and a tube 434, 534 which defines a second chamber 464, 564 and which are connected together by a plurality of transfer chambers which houses a valve structure 470, 570, as described herein with respect to each embodiment of the fluid feed device 420, 520, to allow selective communication of a fluid medium 466, 566 which is housed within each of the chambers. In each embodiment, a front end of the tube 434, 534 is attached to the transfer chambers and a rear end of the cylinder 432, 532 is attached to the transfer chambers, as described herein, by suitable means, such as adhesive, to provide a unitary assembly. The cylinder 432, 532, tube 434, 534 and transfer chambers are made of a suitable material, such as plastic. The tube 434, 534 and the cylinder 432, 532 in each embodiment house like elements to that described with respect to the third embodiment shown in FIGS. 11–18, except for differences noted herein. Thus, a repetition of those like elements is not described herein and instead, the like elements are denoted in the drawings with like references numerals.

One significant difference between the third embodiment of the fluid feed or infusion device 320 and the fourth and fifth embodiments of the fluid feed device 420, 520 is that the device 420, 520 is U-shaped instead of a straight-through device as shown in the third embodiment of the device 320. This provides for a more compact design so as to take up less space while still providing all of the benefits of the straight-through design.

Turning now to the specifics of the fourth embodiment of the fluid feed device 420 as shown in FIGS. 19 and 20, the device 420 includes a first transfer chamber 401, which accommodates the rapid flow of the fluid medium 466 from chamber 462 to chamber 464 when the device 420 is initially cocked or disposed in the ready position, a second composite transfer chamber 403 and a third transfer chamber 405 which provides for the metered flow of the fluid medium 466 from the first chamber 462 defined in the cylinder 432 and the second chamber 464 defined in the tube 434 when the spring 458 expands and it is desired to infuse medication from the syringe 22. A fluid medium 466 of known characteristics, like that used in the previous embodiments, completely fills all of the chambers 462, 464, 401, 403, 405 in the device 420.

The second and third transfer chambers 403, 405 in effect cooperate and are separated from each other by an intermediate wall member 407. The first transfer chamber 401 is the same size as the combined sizes of the second and third transfer chambers 403, 405 and is proximate to the transfer chambers 403, 405. The first transfer chamber 401 is completely separated from the second and third transfer chambers 403, 405 by a wall member 409 so that there is no fluid communication between the first transfer chamber 401 and the second and third transfer chambers 403, 405. A metering orifice provided by tube 478, like that of the previous embodiments, extends through the wall member 407 to provide fluid communication between the second and third transfer chambers 403, 405.

A second or rear end of the cylinder 432 is connected to both the first transfer chamber 401 and the third transfer chamber 405 by the side walls of those chambers. The rear end of the cylinder 432 is substantially closed by the side walls of the transfer chambers 401, 405 with the exception of apertures or ports 411 through the side wall between the cylinder 432 and the first transfer chamber 401 and the single, cord shaped aperture or port 413 through the side wall between the cylinder 432 and the third transfer chamber 405. The ports 411 have a one-way flapper or umbrella valve 415 disposed thereover to allow the passage of fluid medium 466 only from the first chamber 462 in the cylinder 432 into the first transfer chamber 401 but not in the opposite direction. The port 413 allows for the free communication of fluid medium 466 from the first chamber 462 in the cylinder 462 into the third transfer chamber 405 and vice versa.

A first or front end of the tube 434 is connected to both the first transfer chamber 401 and the second transfer chamber 403 by the side walls of those chambers. The front end of the tube 434 is substantially closed by the side walls of the transfer chambers 401, 403 with the exception of apertures or ports 417 through the side wall between the tube 434 and the first transfer chamber 401 and the port 419 through the side wall between the tube 434 and the second transfer chamber 403. The ports 417 have a one-way flapper or umbrella valve 423 thereover to allow the passage of fluid only from the first transfer chamber 401 into the second chamber 464 in the tube 434, but not in the opposite direction. The port 419 allows for the free communication of fluid medium 466 from the first chamber 462 in the cylinder 462 into the second transfer chamber 403 and vice versa.

The method of operation of the fourth embodiment 420 is similar to that as described above with respect to the third embodiment 320, except for the operation and construction of the transfer chamber 401; 403 and 405 and the path of fluid flow therethrough. As such, only the path of the fluid flow is described with respect to the fourth embodiment of the device 420.

As the drive component 452 is pushed rearwardly into the cylinder 432, pressure is applied to the fluid medium 466 housed within the first chamber 452 and causes the fluid medium 466 to open the flapper valve 415 and flow through the apertures 411 and into the first transfer chamber 401. Some fluid medium will flow through the port 413 and into the third transfer chamber 405 and then through the metering orifice provided by tube 478 and into the second transfer chamber 403.

After the fluid medium 466 has passed into the first transfer chamber 401, the pressure from the fluid medium 466 flowing into the first transfer chamber 401 forces the flapper valve 423 open and the fluid medium 466 passes through the apertures 417 and into the second chamber 464. As the fluid medium 466 passes into the second chamber 464, the pressure from the fluid medium 466 drives the piston member 456 backwardly which causes the spring 458 to compress between the piston member 456 and the endcap 444. Once rearward movement of the drive component 452 is stopped, pressure from the fluid medium 466 is no longer being applied to the umbrella valves 415, 423 and the valves 415, 423 close ports 411 and 417 to prevent the passage of fluid medium 466 therethrough.

When the spring 458 is allowed to expand, viz., when the stopcock (not shown) is opened, the piston member 456 moves forwardly in the tube 434 and forces the fluid medium 466 in the second chamber 464 through the port 419 and into the second transfer chamber 403. It is to be noted that under these conditions, fluid pressure will seat the umbrella valve over ports 417 to close the ports. The fluid medium 466 then passes from chamber 403 through the metering orifice provided by tube 478 and into the third transfer chamber 405. Thereafter, the fluid medium 466 flows from the third transfer chamber 405 through the port 413 and into the first chamber 462 in the cylinder 432 which causes the drive component 452 to move relative to the cylinder 432 and depress the plunger portion 26 into the main body portion 24 of the syringe 22 thereby dispensing the medication or drug from the syringe 22. This action places a positive pressure on the syringe 22 to dispense the drug from therewithin. The fluid medium 466 cannot flow through the one-way umbrella valves 415, 423 since the valves are sealed against the side wall of the first transfer chamber 401. In addition, pressure is applied to the umbrella valves 415, 423 by the fluid medium 466 which ensures that the valves remains sealed against the side wall of the first transfer chamber 401.

In this fourth embodiment of the device 420, the movement between chambers is greater than one-to-one since the diameter of the cylinder 432 is smaller than the diameter of the tube 434. It is to be understood, however, that a one-for-one ratio could be achieved if desired by making the chambers the same diameter. Further, since in this embodiment, as in all of the previously discussed embodiments, we are dealing with a closed system for the fluid medium 466, the piston 456 can only move at a rate determined by the rate of flow of the fluid medium through metering orifice provided by tube 478. Correspondingly, the rate of movement of the drive component 452 is also dependent upon the rate of flow through the metering tube. The rate of movement of drive component 452 controls the rate of movement of syringe plunger 26.

Now directing attention to the specifics of the fifth embodiment of the present invention, shown in FIGS. 21 and 22, the device 520 is similar to device 420 described above, except for the construction of the transfer chambers which controls flow of the fluid medium during cocking of the device and also during operation. In this regard the device 520 will not be described in its entirety, but primarily only with respect to the transfer chambers. The device 520 includes first, second, third, fourth and fifth transfer chambers denoted by the references numerals 551, 553, 555, 557 and 559, respectively, which connect the first chamber 562 defined in the cylinder 532 and the second chamber 564 defined in the tube 534 together. A fluid medium 566 of known characteristics, like that of the one used in the previous embodiments, completely fills all of the chambers 562, 564, 551, 553, 555, 557 and 559 in the device 520.

The first and fifth transfer chambers 551, 559 are the same size and are adjacent to each other and are separated from each other by an intermediate wall member 561. A metering orifice provided by tube 578, similar to the one used in the previous embodiments, extends through the wall 561 to provide a fluid communication between the transfer chambers 551, 559. Transfer chamber 551 and 559 along with the metering tube 578 provide for interconnection of the chamber 564 and 562 when the device is operated to dispense medication, as will be explained.

The second transfer chamber 553 is proximate to the first and fifth transfer chambers 551, 559. The first and second transfer chambers 551, 553 are in fluid communication with each other through an aperture or port 563 through the wall which separates the chambers 551, 553. The second and fifth transfer chambers 553, 559 are not in fluid communication with each other and are completely separated from each other by the wall between the chambers.

The second and third transfer chambers 553, 555 are approximately the same size and are separated from each other by a wall member 565 which has an apertures or ports 567 therethrough. A one-way umbrella or flapper valve 569 is seated to overlie the ports 567. The third and fourth transfer chambers 555, 557 are separated from each other by a wall 571 which has apertures or ports 573 therethrough to allow fluid communication between the chambers 555, 557. A one-way umbrella or flapper valve 575 is seated the ports 573. The second flapper valve 575 provides a redundant, or back-up seal for safety purposes to prevent the leakage of fluid medium 566 between the transfer chambers.

The rear portion of the cylinder 532 is connected to the first transfer chamber 551 by the side wall of the transfer chamber 551. The rear end of the cylinder 532 is substantially closed by the side wall of the transfer chambers 551 with the exception of a cord shaped aperture or port 577 through the side wall between the cylinder 532 and the first transfer chamber 551. The port 577 allows for the free communication of fluid medium 566 from the first chamber 562 in the cylinder 562 into the first chamber 551 and vice versa.

A first or forward end of the tube 534 is connected to the fourth and fifth transfer chambers 557, 559 through the side walls of the chambers. The front end of the tube 534 is substantially closed by the side walls of the transfer chambers 557, 559 with the exception of an aperture or port 579 through the side wall opening into the fourth chamber 557 and an aperture or port 581 through the side wall between the tube 534 and the fifth transfer chamber 559. The ports 579, 581 allow for the free communication of fluid medium 566 between the chamber 562 in the tube 564 and the fourth transfer chamber 557, and the chamber 562 in the tube 564 and the fifth transfer chamber 559, respectively.

The method of operation of the infusion pump 520 is similar to that as has been described in detail with respect to the third embodiment of the device 320 and, as such, only the path of movement of the fluid through the transfer chambers is described hereafter with respect to the fifth embodiment of the device 520. As the drive component 552 is pushed rearwardly into the cylinder 532, pressure is applied to the fluid medium 566 housed within the first chamber 562 in the cylinder 532 and causes the fluid medium 566 to flow through the port 577 into the first transfer chamber 551. Some fluid medium 566 may flow through the metering tube 578 and into the fifth chamber 559, but this is minimal.

After entering the first transfer chamber 551, the fluid medium 566 then flows through the port 563 into the second transfer chamber 553. The fluid pressure on the flapper valve 569 causes the valve 569 to open and the fluid medium 566 flows through the apertures 567 and into the third transfer chamber 555. Here again, the fluid pressure on the flapper valve 575 causes the back-up valve 575 to open and the fluid medium 566 will then flow through the aperture 573 and into the fourth transfer chamber 557. Thereafter, the fluid medium 566 flows into the second chamber 564 housed in the tube 534 through the port 579 to move the piston 556 and compress the spring (not shown). Once rearward movement of the drive component 552 is stopped, pressure from the fluid medium 566 is no longer being applied in a manner to open the umbrella valves 567, 574 and the valves 567, 575 close to prevent the passage of fluid medium 566 therethrough in the reverse direction from that discussed above.

When the spring is allowed to expand, this causes the piston member 356 to move forwardly in the tube 534 and forces the fluid medium 566 in the second chamber 564 through the port 581 and into the fifth transfer chamber 559. The fluid will flow only through port 581 as the umbrella valves 575 and 569 are in the closed position and in the transfer chamber 557 is filled with the liquid medium, and as such the fluid medium will not flow through port 579. The fluid medium 566 then passes from the fifth chamber 559 through the metering orifice provided by tube 578 and into the first transfer chamber 551. Thereafter, the fluid medium flows from the first transfer chamber 551 through the port 577 and into the first chamber 562 in the cylinder 532 which causes the drive component 552 to move relative to the cylinder 532 and depress the plunger portion 26 into the main body portion 24 of the syringe 22 thereby dispensing the medication or drug from the syringe 22.

In this embodiment, there may be a tendency for fluid medium 566 to flow through the port 563 into the second transfer chamber 553 after the fluid medium 566 has passed through the metering tube 578. The pressure from this fluid, however, is not great enough to unseal the one-way valves 567, 575 since the pressure from the fluid medium 566 on the other side of the valve 575, due to the pressure created on the fluid medium 566 by the spring expanding, is greater than the pressure being applied to the underside of the valves 567, 575.

In each of the above-described embodiments, since the metering tube is of a predetermined length and diameter, the spring is of a known spring force and the fluid medium has known characteristics, the fluid medium can only pass through the metering orifice at a set rate which, in turn, dispenses the medication or drug from the syringe over a predetermined time period. By varying these known factors, the fluid medium can pass through the metering orifice at a faster or slower rate depending what is desired. For example, the viscosity of the fluid medium, the strength of the spring or the diameter of the metering tube could be changed to vary the rate. In addition, the diameter of the syringe needle can be varied to control the rate that the liquid product is dispensed from the syringe. For example, five different syringe needle diameters could be used with a single fluid feed device of the present invention to achieve five different rates at which the liquid product is expelled from the syringe.

It is also noted that while one-way umbrella or flapper valves are described hereinabove, it is to be understood that a suitable manually actuated valve or valves could instead be employed. Additionally, while a spring 158–458 is used and disclosed hereinabove as the biasing or driving structure, it to be understood that other stored biasing or driving structure could be used to accomplish the above-described function, such as compressed gas. Further, while the drive component is moved into the cylinder by the plunger portion of the syringe, it is to be understood that the drive component could instead be moved by an outside object.

The novel fluid feed device of the present invention reliably dispenses medication or a drug to a patient at a predetermined rate over a predetermined time period. It is compact and lightweight and allows a patient to be ambulatory and move around. It does not rely on the characteristics of the medication to dispense the drug medication. In addition, the present invention can be used and reused over and over again without sacrificing reliability.

It is to be noted that while the novel fluid feed device of the present invention is disclosed as being used in a fluid infusion or intravenous application, it is to be understood that the fluid feed device could be used in other applications. For example, the fluid feed device of the present invention could be used as a timer for opening or closing a valve.

While preferred embodiments of the present invention are shown and described, it is envisioned that those skilled in the art may devise various modifications of the present invention without departing from the spirit and scope of the appended claims.

The invention claimed is:

1. A fluid infusion pump device capable of use in an infusion application of a liquid product from a syringe of the general type which includes a main body portion housing the liquid product and a plunger portion for movement to expel the liquid product from the syringe, said device comprising:

- a housing including a compartment for reception of at least the plunger portion of the syringe;
- a drive component relatively movable with respect to said compartment and being engaged with the plunger portion of the syringe;
- a piston member relatively movable with respect to said housing,
- a fluid medium contained within said housing and being in direct communication with said drive component and said piston member and being between said drive component and said piston member;
- biasing means for biasing said piston member in a first direction of movement to impart a force on said fluid medium;
- metering means in communication with said fluid medium and through which said fluid medium can pass upon movement of said piston member in said first direction, said metering means restricting and controlling the flow of said fluid medium upon movement of said piston member in said first direction, such that the movement of said piston member in said first direction directly acts on and imparts a force on said fluid medium causing said fluid medium to directly act on and impart movement to said drive component, thereby causing said drive component to move and to produce movement of said plunger portion of the syringe with the metering means controlling the rate of movement of said piston member and said drive component and correspondingly the movement of said plunger portion, thereby controlling the rate of expulsion of liquid product from the syringe.

2. A fluid pump device as defined in claim 1, further including first and second chambers in said housing for holding said fluid medium therein, said first and second chambers being separated by a barrier and being in fluid communication with each other, said drive component and said barrier defining said first chamber, said piston member and said barrier defining said second chamber, said metering means being in communication across said barrier for providing fluid communication between said first and second chambers and through which said fluid medium can pass from said second chamber to said first chamber upon movement of said piston member in said first direction.

3. A fluid pump device as defined in claim 2, wherein said biasing means comprises a spring interengaged between said drive component and said first and second chambers.

4. A fluid pump device as defined in claim 3, further including an elongate rod interengaged between said drive component and said piston member.

5. A fluid pump device as defined in claim 1, wherein said biasing means comprises a spring interengaged between said piston member and a wall of said housing.

6. A fluid pump device as defined in claim 2, wherein said first and second chambers have a passageway therebetween, and valve structure selectively blocking said passageway to prevent the flow of fluid medium therethrough from said second chamber to said first chamber yet permitting the rapid return movement of said piston member in a second direction opposite said first direction.

7. A fluid pump device as defined in claim 6, wherein said piston member separates said first and second chambers from each other.

8. A fluid pump device as defined in claim 7, wherein said passageway is through said piston member, said passageway allowing the fluid medium to flow through said piston member from said first chamber to said second chamber when said passageway is not blocked by said valve structure, said valve structure comprising a plate member normally biased against said piston member to block said passageway and to prevent the flow of said fluid medium through said piston member, said plate member being biased away from said piston member to open said passageway and to allow said fluid medium to flow through said piston member when said piston member is moved in said second direction.

9. A fluid pump device as defined in claim 8, wherein said plate member is biased away from said piston member when said piston member is moved in said second direction by action of said fluid medium against said plate member.

10. A fluid pump device as defined in claim 8, wherein said plate member is normally biased against said piston member by a valve spring.

11. A fluid pump device as defined in claim 1, wherein said metering means is provided by a metering tube.

12. A fluid pump device as defined in claim 8, wherein said metering orifice is in communication between said first and second chambers to allow fluid medium to pass from said second chamber to said first chamber upon movement of said piston member in said first direction.

13. A fluid pump device as defined in claim 12, wherein said metering orifice extends through said piston member and said plate member to allow fluid medium to pass therethrough upon movement of said piston member in said first direction.

14. A fluid pump device as defined in claim 2, wherein said metering orifice provides operative communication between said first and second chambers to allow fluid medium to pass from said second chamber to said first chamber upon movement of said piston member in said first direction.

15. A fluid pump device as defined in claim 1, wherein said liquid medium is selected from a group including mineral oil or medical silicone.

16. A fluid pump device as defined in claim 6, further including at least one transfer chamber through which said fluid medium flows in moving from said first chamber to said second chamber or from said second chamber to said first chamber when said piston member is moved in one of said first direction or said second direction.

17. A fluid pump device as defined in claim 16, wherein said metering means provides operative communication between said second chamber and said first chamber.

18. A fluid pump device as defined in claim 17, wherein said valve structure blocks said passageway by being biased into a seated position in said passageway.

19. A fluid pump device as defined in claim 18, wherein said valve structure is biased into said seated position by a spring.

20. A fluid pump device as defined in claim 17, further including a return passageway which is operatively interconnected between said first and second chambers to allow fluid medium to flow therethrough when said piston member is moved in said first direction and in said second direction.

21. A fluid pump device as defined in claim 6, further including a manually actuated member which can be actuated to move said valve structure to unblock said passageway between said first and second chambers so that said fluid medium can flow from said first chamber into said second chamber.

22. A fluid pump device as defined in claim 21, wherein said barrier includes a transfer chamber between said first chamber and said second chamber and through which said fluid medium flows through from said first chamber to said second chamber when said piston member moves in said second direction.

23. A fluid pump device as defined in claim 22, wherein said metering orifice is positioned between said second chamber and said transfer chamber.

24. A fluid pump device as defined in claim 23, wherein said valve structure normally blocks said passageway by being biased into a seated position in said passageway.

25. A fluid pump device as defined in claim 23, further including a return passageway which is operatively interconnected between said first and second chambers to allow fluid medium to flow therethrough when said piston member is moved in said first direction and said second direction.

26. A fluid pump device as defined in claim 6, wherein said valve structure comprises a plunger which can be selectively biased to block said passageway between said first and second chambers.

27. A fluid pump device as defined in claim 26, wherein said plunger can be actuated by an object external to the fluid pump device, such as a user's finger, to open said passageway to allow fluid communication between said first chamber and said second chamber.

28. A fluid pump device as defined in claim 26, further including at least one transfer chamber separating said first and second chambers, said passageway being defined through said at least one transfer chamber, said fluid medium passing from said first chamber through said at least one transfer chamber to said second chamber when said piston member is moved in one of said first or second directions.

29. A fluid pump device as defined in claim 26, wherein said metering means passes fluid medium from said second chamber to said first chamber when said piston member is moved in said first direction.

30. A fluid pump device as defined in claim 29, wherein said metering means is provided by a metering tube offset from said plunger so as to always allow fluid medium to pass through said metering tube.

31. A fluid pump device as defined in claim 6, wherein said valve structure comprises at least one one-way valve to allow fluid to pass from said first chamber to said second chamber when said drive component is moved in a second direction opposite to said first direction of movement of said piston member.

32. A fluid pump device as defined in claim 16, wherein said valve structure comprises at least one one-way valve to allow fluid medium to pass from said first chamber through said transfer chamber to said second chamber when said piston member is moved in said second direction.

33. A fluid pump device as defined in claim 32, wherein said fluid medium acts directly on said drive component to move said drive component in said first direction.

34. A fluid pump device as defined in claim 6, further including a number of transfer chambers through which said fluid medium flows through from said first chamber to said second chamber and from said second chamber to said first chamber.

35. A fluid pump device as defined in claim 34, wherein said metering orifice is positioned between two of said transfer chambers to provide an operative communication between said first chamber and said second chamber when said piston member is moved in said first direction.

36. A fluid pump device as defined in claim 35, wherein said transfer chambers include a first port which operatively connects said first chamber and one of said transfer chambers together and a second port which operatively connects said second chamber and one of said transfer chamber together to allow fluid medium to flow therethrough when said piston member is moved in said first direction.

37. A fluid pump device as defined in claim 36, wherein said valve structure comprises a one-way valve which operatively interconnects said first chamber and one of said transfer chambers together and a one-way valve which operatively connects said second chamber and one of said transfer chamber together to allow fluid medium to flow therethrough when said piston member is moved in said second direction.

38. A fluid pump device as defined in claim 37, wherein said transfer chambers through which said fluid medium flows when said piston member moves in said first direction are separated from said transfer chambers through which said fluid medium flows when said piston member moves in said second direction.

39. A fluid pump device as defined in claim 1, further including structure for attaching the syringe to said housing.

40. A fluid pump device as defined in claim 39, wherein said attaching structure comprises a locking cap.

41. A fluid pump device as defined in claim 40, wherein said attaching structure further including lugs, which ears on the syringe engage when the syringe is attached to said housing.

42. A fluid pump device as defined in claim 1, wherein said housing is U-shaped.

43. A fluid pump device capable of use in an infusion application of a liquid product from a syringe of the general type which includes a main body portion housing the liquid product and a plunger portion for movement to expel the liquid product from the syringe, said fluid pump device comprising:
- a housing including a compartment for reception of at least the plunger portion of the syringe;
- a drive component relatively movable with respect to said compartment and engaged with the plunger portion of the syringe;
- a piston member relatively movable with respect to said housing;
- said housing having a first chamber and a second chamber therein, said first and second chambers being in fluid communication with each other and with said drive component;
- a fluid medium contained within and completely filling said first and second chambers and being between said drive component and said piston member;
- first means for passing at least a portion of said fluid medium from said first chamber to said second chamber when said drive component is moved into said housing; and
- second means for passing at least a portion of said fluid medium from said second chamber to said first chamber when said drive component is moved relative to said housing, said second means restricting and controlling the rate of passage of said fluid medium from said second chamber to said first chamber such that when piston member acts directly on and pressurizes said fluid medium, said fluid medium is passed from said second chamber to said first chamber and said fluid medium acts directly on said drive component to move said drive component at a predetermined rate to depress the plunger portion into the syringe body to expel the liquid product from the syringe.

44. A fluid pump device as defined in claim 40, wherein said first means comprises a valve structure which selectively allows fluid medium to pass from said first chamber to said second chamber.

45. A fluid pump device as defined in claim 44, wherein said valve structure can be moved by an object external to the fluid pump device, such as a user's finger, to move said valve structure into a position which prevents movement of the fluid medium from said first chamber to said second chamber.

46. A fluid pump device as defined in claim 44, wherein said valve structure comprises a predetermined number of one-way valves which only allow flow of fluid medium from said first chamber to said second chamber.

47. A fluid pump device as defined in claim 46, further including at least one transfer chamber through which said fluid medium passes from said first chamber to said second chamber, said one-way number of valves selectively allowing fluid communication between said first chamber and one of said transfer chambers, and between said second chamber and one of said transfer chambers.

48. A fluid pump device as defined in claim 47, wherein said second structure comprises a metering orifice, said metering orifice providing fluid communication between two of said transfer chambers.

49. A fluid pump device as defined in claim 43, wherein said second means comprises a metering orifice.

50. A fluid infusion system including a pump device and a syringe capable of use in an infusion application of a liquid product from said syringe, which syringe includes a main body portion housing the liquid product and a plunger portion for movement relative thereto to expel liquid product from said syringe, said pump device comprising, a housing including a compartment for reception for at least a plunger portion of said syringe; a fluid medium contained within said housing and movable under pressure across a barrier through a metering means, said metering means for providing fluid communication across said barrier; a piston member for pressurizing said fluid medium; biasing means for urging said piston member in a first direction to act directly on and pressurize said fluid medium; and a drive component relatively movable with respect to said compartment and engaged with said syringe plunger portion, said fluid medium being between said drive component and said piston member, said drive component operably applying the movement of said piston member to said syringe plunger portion wherein the rate of movement of said piston member is determined by the movement of said fluid medium through said metering means which in turn determines the rate of movement of said syringe plunger portion, said piston member acting directly on and pressurizing said fluid medium such that said fluid medium acts directly on said drive component to produce corresponding movement of said syringe plunger portion.

51. A system according to claim 50, wherein said piston member and said drive component are interconnected for associated coordinated movement.

52. A system according to claim 50, wherein said drive component is a second piston member.

53. A system according to claim 50, wherein the main body portion of said syringe includes an outlet end and an opposite end, and said housing includes structure for receiving, engaging and retaining said opposite end of the syringe.

54. A system according to claim 53, wherein said opposite end of the syringe includes an engagement structure for engaging said syringe with said housing, and said housing defines an opening of complimentary shape to said engagement structure and includes a locking cap thereon for receiving and engaging said engagement structure.

55. A system according to claim 53, wherein said locking cap is rotatable and is engaged with said housing in a manner to produce relative linear movement of said locking cap to clamp said syringe in place.

56. A system according to claim 50, further including valve structure associated with said barrier which is opened upon movement of said drive component in a second direction opposite to said first direction of movement of said piston member to permit rapid return movement of said piston member against the force of said biasing means.

57. A system according to claim 50, wherein said housing further includes structure for fixing said syringe in place with respect to said housing.

58. A system according to claim 50, wherein said housing includes a fluid containing cylinder portion, said piston member being disposed and relatively movable within said fluid containing cylinder portion to separate said fluid containing cylinder portion into first and second fluid containing chambers, with said piston member providing said barrier and said metering orifices being provided through said piston member to control the rate of movement of said piston member in said first direction.

59. A system according to claim 58, further including valve structure for bypassing said metering orifice to permit rapid movement of fluid medium across said barrier provided by said piston member.

60. A system according to claim 58, wherein there is provided a drive component disposed in and relative movable with respect to said housing compartment for engaging said syringe plunger portion.

61. A system according to claim 60, wherein there is provided a rod member interconnecting said drive component and said piston member.

62. A system according to claim 50, further including a transfer chamber formed in said barrier separating said first and second chambers and valve structure providing for the control of fluid communication between said first and second chambers.

63. A method of providing for the control rate of introduction of a medication from a syringe, said method including the steps of: providing a syringe with a known volume of medication and including a plunger portion; providing a fluid pump and engaging said syringe plunger portion with said pump, which pump includes a closed fluid system employing a fluid medium having known fluid flow characteristics and having a piston member and a drive component, said fluid medium being between said drive component and said piston member, said drive component being engaged with said syringe plunger portion; pressurizing said fluid medium by imparting movement to said piston member to force said fluid medium through a metering tube associated with said piston member; selecting the size of said metering tube and the amount of pressure applied to said fluid medium to attain a desired rate of flow of said fluid medium through said metering tube; and using the flow of said fluid medium through said metering tube to control the rate of movement of said syringe plunger portion, and correspondingly the rate of expulsion of medication from said syringe, said piston member acting directly on said fluid medium to pressurize said fluid medium and said fluid medium acting directly on said drive component to cause movement of said syringe plunger portion.

64. A pump device comprising: a housing; a fluid medium contained within said housing; a drive component relatively movable with respect to said housing and in direct communication with said fluid medium; a relatively movable piston member in direct communication with said fluid medium; said fluid medium being between said drive component and said piston member; and biasing means for biasing said piston member in a first direction of movement to directly impart a force on said fluid medium; a metering orifice in communication with said fluid medium and through which said fluid medium can pass upon movement of said piston member in said first direction, said metering orifice restricting and controlling the flow of said fluid medium upon movement of said piston member in said first direction, such that the movement of said piston member in said first direction pressurizes and acts directly on said fluid medium and said fluid medium acts directly on said drive component to move said drive component with the metering orifice controlling the rate of movement of said piston member and said drive component.

65. A pump device as defined in claim 64, wherein said device is used to actuate a valve when said drive component is moved.

66. A pump device as defined in claim 64, wherein said device is used to depress a plunger portion of a syringe into the syringe to expel a liquid product from the syringe at a controlled rate.

* * * * *

UNITED STATES PATENT AND TRADEMARK OFFICE
CERTIFICATE OF CORRECTION

PATENT NO. : 5,788,673
DATED      : August 4, 1998
INVENTOR(S) : Larry Lee Young, Richard Rabenau, Stephen Perry Lisak and Rowland William Kanner It is certified that error appears in the above-indentified patent and that said Letters Patent is hereby corrected as shown below:

Column 4, Line 38 "device 120 capable" should be -- device capable --

Column 25, Line 56 "one-way number" should be -- number of one-way --

Signed and Sealed this

Sixteenth Day of March, 1999

Attest:

Attesting Officer

Q. TODD DICKINSON

Acting Commissioner of Patents and Trademarks